United States Patent
Komiya et al.

(10) Patent No.: US 10,208,333 B2
(45) Date of Patent: Feb. 19, 2019

(54) SEQUENCE CONVERSION AND SIGNAL AMPLIFIER DNA HAVING LOCKED NUCLEIC ACIDS AND DETECTION METHODS USING SAME

(71) Applicants: ABBOTT LABORATORIES, Abbott Park, IL (US); TOKYO INSTITUTE OF TECHNOLOGY, Tokyo (JP)

(72) Inventors: Ken Komiya, Tokyo (JP); Makoto Komori, Matsudo (JP); Toru Yoshimura, Matsudo (JP)

(73) Assignees: Abbott Laboratories, Abbott Park, IL (US); Tokyo Institute of Technology, Tokyo (JP)

( * ) Notice: Subject to any disclaimer, the term of this patent is extended or adjusted under 35 U.S.C. 154(b) by 0 days.

(21) Appl. No.: 14/882,124

(22) Filed: Oct. 13, 2015

(65) Prior Publication Data

US 2016/0102339 A1    Apr. 14, 2016

Related U.S. Application Data

(60) Provisional application No. 62/063,666, filed on Oct. 14, 2014, provisional application No. 62/098,066, filed on Dec. 30, 2014.

(51) Int. Cl.
C12Q 1/68 (2018.01)
C12Q 1/682 (2018.01)
C12Q 1/6844 (2018.01)

(52) U.S. Cl.
CPC .......... *C12Q 1/682* (2013.01); *C12Q 1/6844* (2013.01)

(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,800,159 | A | 1/1989 | Mullis et al. |
| 5,958,700 | A | 9/1999 | Nadeau et al. |
| 6,316,200 | B1 | 11/2001 | Nadeau et al. |
| 9,845,495 | B2 | 12/2017 | Komiya |
| 2003/0082590 | A1 | 5/2003 | Van Ness et al. |
| 2003/0165911 | A1 | 9/2003 | Van Ness et al. |
| 2004/0259102 | A1 | 12/2004 | Kool |
| 2005/0059005 | A1 | 3/2005 | Tuschl et al. |
| 2008/0311564 | A1 | 12/2008 | Fort |
| 2009/0017453 | A1 | 1/2009 | Maples et al. |
| 2009/0081670 | A1 | 3/2009 | Maples et al. |
| 2010/0129822 | A1 | 5/2010 | Siva |
| 2014/0017692 | A1 | 1/2014 | Komiya |
| 2015/0197823 | A1 | 7/2015 | Komiya et al. |
| 2016/0102345 | A1 | 4/2016 | Komiya et al. |

FOREIGN PATENT DOCUMENTS

| | | |
|---|---|---|
| CN | 103789435 | 5/2014 |
| EP | 1500710 | 1/2005 |
| EP | 2722399 | 4/2014 |
| JP | H07114718 A | 5/1995 |
| JP | H07114718 B2 | 12/1995 |
| JP | 2005516610 | 6/2005 |
| WO | 200028082 | 5/2000 |
| WO | 200216639 | 2/2002 |
| WO | 2003066802 | 8/2003 |
| WO | 2004067726 | 8/2004 |
| WO | 2004067764 | 8/2004 |
| WO | 2004067765 | 8/2004 |
| WO | 2008001376 | 1/2008 |
| WO | 2009012246 | 1/2009 |
| WO | 2012077819 | 6/2012 |
| WO | 2015114469 | 8/2015 |
| WO | 2016059473 | 4/2016 |
| WO | 2016059474 | 4/2016 |

OTHER PUBLICATIONS

Lai et al., "Calibration Curves for Real-Time PCR", Clinical Chemistry 51:7, pp. 1132-1136, 2005, Molecular Diagnostics and Genetics.
Tan, E. et al., "Isothermal DNA Amplification with Gold Nanosphere-Based Visual Calorimetric Readout for Herpes Simplex Virus Detection", Clinical Chemistry, 53, No. 11, pp. 2017-2020 (2007).
Tan, E. et al., "Isothermal DNA Amplification Coupled with DNA Nanosphere-Based Colorimetric Detection", Analytical Chemistry, vol. 77, No. 24, pp. 7984-7992 (Dec. 15, 2005).
Tan, E. et al., "Specific versus Nonspecific Isothermal DNA Amplification through Thermophilic Polymerase and Nicking Enzyme Activities", Biochemistry, vol. 47, No. 38, pp. 9987-9999 (2008).
G.T Walker, M.C. Little, J.G. Nadeau and D.D. Shank, Proc. Natl. Acad.Sci.USA,89, 392-396 (1992).
Y Weizmann, M.K. Beissenhirtz, Z. Cheglakov, R.Nowarski and I Willner, Angew. Chem.InI.Ed.,45,7384-7388(2006).

(Continued)

*Primary Examiner* — James Martinell
(74) *Attorney, Agent, or Firm* — Christopher P. Singer, McAndrews, Held & Malloy, Ltd.; Audrey L. Bartnicki

(57) ABSTRACT

Disclosed are methods for detecting a target nucleic acid in a sample. The methods include contacting said sample, in the presence of a polymerase and an endonuclease, with a sequence conversion oligonucleotide having locked nucleic acids at select positions sufficient to decrease non-specific background signal amplification. Also disclosed are methods for detecting a target nucleic acid in a sample in which said sample is contacted, in the presence of a polymerase and an endonuclease, with a sequence conversion oligonucleotide and a signal amplifier oligonucleotide, both having locked nucleic acids at select positions sufficient to decrease non-specific background signal amplification. The disclosure also provides compositions and kits comprising such sequence conversion and signal amplifier oligonucleotides.

10 Claims, 5 Drawing Sheets

Specification includes a Sequence Listing.

(56) References Cited

OTHER PUBLICATIONS

International Preliminary Report, PCT/JP2011/078717, International Filing Date Dec. 12, 2011 (Tokyo Institute of Technology).
J. Van Ness, L.K. Ness, and D.J. Galas, Proc. Natl. Acad. Sci. USA, 100 (8):4504-4509 (Apr. 15, 2003).
Dirks, Robert M., Pierce, Niles A., PNAS, Oct. 26, 2004, vol. 101, No. 43, 15275-15278.
Huang, Jin, Wu, Yanrong, Chen, Van, Zhu, Zhi, Yang, Xiaohai, Yang, Chaoyong James, Wang, Kemin, Tan, Weihong, Angew. Chem.Inl.Ed. 2011,50,401-404.
Niu, Shuyan, Jiang, Yu, Zhang, Susheng, Chem. Commun., 2010, 46, 3089-3091 (2010).
International Search Report, PCT/JP2011/078717, International Filing Date Dec. 12, 2011 (Tokyo Institute of Technology).
International Search Report and Written Opinion of PCT Patent Application No. PCT/IB2015/000726, dated Sep. 10, 2015.
Gill, et al. "Nucleic Acid Isothermal Amplification Technologies—A Review", Nucleosides, Nucleotides and Nucleic Acids, Taylor & Francis, US, vol. 27, No. 3, Mar. 1, 2008, pp. 224-243.
Veedo et al., "Locked Nucleic Acids: Promising Nucleic Acid Analogs for Therapeutic Applications," Chemistry & Biodiversity, vol. 7, 2010, 7 pages, pp. 536-542.
Yang et al., "Synthesis and investigation of deoxyribonucleic acid/locked nucleic acid chimeric molecular beacons," Nucleic Acids Research, vol. 35, 2007, 9 pages, pp. 4030-4041.
Vester et al., "LNA (Locked Nucleic Acid): High-Affinity Targeting of Complementary RNA and DNA," Biochemistry, vol. 43, 2004, 12 pages, pp. 13233-13241.
PCT International Search Report and Written Opinion dated Mar. 29, 2016 for PCT Patent Application No. PCT/IB2015/002145.
PCT, Notification of Transmittal of the International Search Report and the Written Opinion of the International Searching Authority, or the Declaration, in International Application No. PCT/IB2015/059986, dated Jun. 3, 2016 (16 pages).
Haiyun Liu et al., "High Specific and Ultrasensitive Isothermal Detection of MicroRNA by Paddlock Prob-Based Exponential Rolling Circle Amplification", Analytical Chemistry, vol. 85, No. 16, Aug. 20, 2013 (Aug. 20, 2013), pp. 7941-7947, XP055272748, ISSN: 0003-2700, DOI:10.1021/ac401715k abstract (7 pages).
Bin-Cheng Yin et al., "Sensitive Detection of MicroRNA in Complex Biological Samples via Enzymatic Signal Amplification Using DNA Polymerase Coupled with Nicking Endonuclease" Analytical Chemistry, vol. 85, No. 23, Dec. 3, 2013 (Dec. 3, 2013), pp. 11487-11493, XP055272740, ISSN: 0003-2700, DOI: 10.1021/ac403302a abstract (7 pages).
International Search Report and Written Opinion of PCT Patent Application No. PCT/IB2015/002141, dated Apr. 6, 2016, 8 pages.
International Bureau, "International Preliminary Report on Patentability", issued in connection with Application No. PCT/IB2015/002141, dated Apr. 18, 2017, 6 pages.
International Bureau, "International Preliminary Report on Patentability", issued in connection with Application No. PCT/IB2015/002145, dated Apr. 18, 2017, 10 pages.
Stratagene Catalog, p. 39 (1988).
Silahtaroglu et al., "Detection of microRNAs in frozen tissue sections by fluorescence in situ hybridization using locked nucleic acid probes and tyramide signal amplification", Nature Protocols, vol. 2, No. 10, Oct. 1, 2007, pp. 2520-2528.

SEQUENCE CONVERSION AND SIGNAL AMPLIFIER DNA HAVING LOCKED NUCLEIC ACIDS AND DETECTION METHODS USING SAME

CROSS-REFERENCE TO RELATED APPLICATIONS

The present application claims the benefit of priority to U.S. Provisional Application 62/063,666, which was filed on Oct. 14, 2014 and to U.S. Provisional Application 62/098,066, which was filed on Dec. 30, 2014. Both U.S. Provisional Applications are incorporated herein by reference in their entireties.

SEQUENCE LISTING

This application contains a Sequence Listing which is incorporated by reference and is submitted with the filing of this application as a text file titled, "12350USL1_SeqList.TXT". The Sequence Listing file was created on Oct. 7, 2014 and is 17,464 bytes in size.

FUNDING

At least a portion of the research disclosed herein was supported by a grant from the Japan Science and Technology Agency (JST), an agency of the Government of Japan.

BACKGROUND

The detection of target nucleic acid in test samples is important in various fields, including medicine and biology. Many compositions, assay platforms, and procedures are available for the detection of specific nucleic acid molecules. In order for detection to be reproducible and accurate, these procedures require no or low levels of non-specific background amplification. However, amplification methods may give rise to false positive signals that affect the quality, accuracy, reproducibility, and overall reliability of the results. In some assays these "false" positive signals can be detected in samples, including control samples that contain non-template DNA (non-target DNA) or even samples that lack any DNA template.

One common method used for amplification of specific sequences from a population of mixed nucleic acid sequences is the polymerase chain reaction (PCR). Since a typical PCR is carried out at three different temperatures, the reaction can be associated with challenges such as difficulty in maintaining accurate temperatures and that the time loss increases in proportion to the number of amplification cycles. The denaturation of a double-stranded template DNA into single strands (while dependent to some extent on the particular sequence) often requires the use of high "melting" temperatures, which limits the class of DNA polymerases that can be used to those that are highly thermostable. Consequently, isothermal amplification platform technologies have been developed to detect nucleic acids under reaction conditions that are milder than those used in PCR. Nevertheless, these isothermal amplification technologies have not addressed the challenges that are presented by non-specific amplification events and high background signals that can interfere with target sequence detection.

The following disclosure provides alternative methods and compositions for detecting a nucleic acid sequence (such as DNA or RNA) under reaction conditions that are less rigorous than those used in PCR. The methods and compositions maintain sequence selectivity and sensitivity that allow for the detection of nucleic acid molecules that may be in a sample at low concentrations and/or nucleic acid molecules of a short length. The methods and compositions also reduce any background signal that may result from non-specific and/or target-independent amplification events. Among other aspects, the disclosure provides novel methods and nucleic acid molecules that can improve the detection limit of target nucleic acids in a sample under low temperature, isothermal conditions, and can simplify or improve sample preparation and automated methods of detection.

SUMMARY OF THE INVENTION

In one aspect, the disclosure relates to a method for detecting a target nucleic acid in a sample, said method comprising contacting said sample with: an oligonucleotide (sequence conversion DNA or SC DNA) comprising, in the 5' to 3' direction, a signal DNA generation sequence (A), an endonuclease recognition site (B), and a sequence (C) complementary to the 3' end of a target nucleic acid, and which has at least one chemically modified nucleotide; a polymerase; and an endonuclease for a nicking reaction. In embodiments of this aspect, the method also comprises determining the presence or absence of a signal DNA, wherein the presence of the signal DNA indicates the presence of the target nucleic acid in the sample.

In one aspect, the disclosure relates to a method for detecting a target nucleic acid in a sample, said method comprising contacting said sample with: a first oligonucleotide (sequence conversion DNA or SC DNA) comprising, in the 5' to 3' direction, a signal DNA generation sequence (A), an endonuclease recognition site (B), and a sequence (C) complementary to the 3' end of a target nucleic acid, and which has at least one chemically modified nucleotide; a second oligonucleotide (signal amplifier DNA or SA DNA) comprising, in the 5' to 3' direction, a signal DNA generation sequence (D) that is homologous to the signal DNA generation sequence (A) of the first oligonucleotide, an endonuclease recognition site (E) (which may be the same or different from the endonuclease recognition site (B) in the SA DNA), and a sequence (F) that is homologous to the signal DNA generation sequence (A) of the first oligonucleotide, and which has at least one chemically modified nucleotide; a polymerase; and an endonuclease for a nicking reaction. In embodiments of this aspect, the method also comprises determining the presence or absence of a signal DNA, wherein the presence of the signal DNA indicates the presence of the target nucleic acid in the sample.

In another aspect, the disclosure relates to a method for detecting a target nucleic acid in a sample, said method comprising contacting said sample with: an oligonucleotide (sequence conversion DNA or SC DNA) comprising, in the 5' to 3' direction, a signal DNA generation sequence (A), an endonuclease recognition site (B), and a sequence (C) complementary to the 3' end of a target nucleic acid, and which has at least one locked nucleic acid (LNA); a polymerase; and an endonuclease for a nicking reaction. In embodiments of this aspect, the method also comprises determining the presence or absence of a signal DNA, wherein the presence of the signal DNA indicates the presence of the target nucleic acid in the sample.

In another aspect, the disclosure relates to a method for detecting a target nucleic acid in a sample, said method comprising contacting said sample with: a first oligonucleotide (sequence conversion DNA or SC DNA) comprising, in the 5' to 3' direction, a signal DNA generation sequence (A), an endonuclease recognition site (B), and a sequence (C) complementary to the 3' end of a target nucleic acid, and which has at least one locked nucleic acid (LNA); a second oligonucleotide (signal amplifier DNA or SA DNA) comprising, in the 5' to 3' direction, a signal DNA generation sequence (D) that is homologous to the signal DNA generation sequence (A) of the first oligonucleotide, an endonuclease recognition site (E) (which may be the same or different from the endonuclease recognition site (B) in the SA DNA), and a sequence (F) that is homologous to the signal DNA generation sequence (A) of the first oligonucleotide, and which has at least one LNA; a polymerase; and an endonuclease for a nicking reaction. In embodiments of this aspect, the method also comprises determining the presence or absence of a signal DNA, wherein the presence of the signal DNA indicates the presence of the target nucleic acid in the sample.

In certain embodiments the LNA present in either sequence (C) of the SC DNA or in sequence (F) of the SA DNA can comprise any LNA such as, for example, G, T, U, A, and C as well as chemically modified derivatives thereof. In embodiments wherein the nucleotide molecules comprise more than one LNA, each LNA may be independently selected from any LNA (e.g., G, T, U, A, and C) as well as chemically modified derivatives thereof or any combinations thereof. In certain embodiments there is at least one LNA located at position 1 to 50, 1 to 45, 1 to 40, 1 to 35, 1 to 30, 1 to 25, 1 to 20, 1 to 15, 1 to 10, or 1 to 5 from the 3'-end of the SA DNA (within sequence (F)), and the SC DNA (within sequence (C)). As discussed further below, the inventors have illustrated certain embodiments of the disclosure that exemplify that including one or more LNAs in the SA DNA, and in the SC DNA, reduces background signals in the performance of the methods disclosed herein (e.g., resulting from target-independent amplification).

In some embodiments incorporating LNAs into sequence (F) of the SA DNA, and into sequence (C) of the SC DNA, can eliminate the generation of non-specific background signals in an amplification reaction. In other embodiments, incorporating LNAs in the SA DNA and SC DNA molecules can delay the generation of non-specific amplification events for a period of time that allows for specific and accurate measurement of target nucleic acid. Thus, the disclosure provides for nucleic acid molecules, compositions, kits, and methods that allow for measurement of signal sequence(s) that indicate the presence of a target nucleic acid before any non-specific interfering background signal is generated. For example, in some embodiments a signal resulting from the presence of from about 1 nM to about 1 fM target nucleic acid in a sample is detectable about 10 to about 120 minutes before any interfering non-specific background signal is detectable.

In certain embodiments the polymerase may have strand displacement activity. In further embodiments, the polymerase may be 3' to 5' exonuclease deficient, 5' to 3' exonuclease deficient, or both 3' to 5' exonuclease deficient and 5' to 3' exonuclease deficient. In some embodiments the polymerase comprises a DNA polymerase.

In embodiments, the endonuclease may comprise a nicking endonuclease or a restriction endonuclease that can be used in a reaction that nicks an oligonucleotide.

While the method disclosed herein may be performed under typical DNA amplification conditions (e.g., typical temperatures associated with standard PCR, reactant concentrations, time cycles, etc.), in some embodiments the method may be performed under isothermal conditions or under substantially constant temperatures. In further embodiments the method may be performed at temperatures that are lower than temperatures used in standard PCR methods. As one example, some embodiments of the method may be performed at a temperature at or below a calculated optimal hybridization or annealing temperature, or an experimentally determined hybridization or annealing temperature, of the target nucleic acid (T) and the sequence (C) of the SC DNA, or of the signal DNA (S) and the sequence (F) of the SA DNA as described below. In embodiments, the method may be performed at a temperature that is below the melting temperature of the target nucleic acid (T) bound to the sequence (C) of the SC DNA, or the signal DNA (S) bound to the sequence (F) of the SA DNA. In yet other embodiments, the method may be performed at temperatures that allow for polymerase and/or endonuclease activity. In further embodiments, the method may be performed at temperatures that are at or about the optimal reaction temperature for the polymerase and/or endonuclease present in the reaction mixture for the detection of a target nucleic acid in a sample.

In another aspect, the disclosure relates to a chemically modified oligonucleotide, which may be referred herein as a "sequence conversion DNA" (or "SC DNA") comprising, in the 5' to 3' direction, a signal DNA generation sequence (A), an endonuclease recognition site (B), and a sequence (C) complementary to the 3' end of a target nucleic acid, and which has at least one locked nucleic acid (LNA).

In another aspect, the disclosure relates to a chemically modified oligonucleotide, which may be referred to herein as a "signal amplifier DNA" (or "SA DNA") comprising, in the 5' to 3' direction, a signal DNA generation sequence (D) homologous to a signal DNA generation sequence (A) of a sequence conversion DNA (SC DNA), an endonuclease recognition site (E), and a sequence having at least one locked nucleic acid (LNA) and which is homologous to a signal DNA generation sequence (A) of a sequence conversion DNA (SC DNA).

The target nucleic acid sequence may be any nucleotide sequence of interest and in some embodiments may comprise a sequence that originates from an infectious agent or a micro-RNA. In other embodiments the target nucleic acid may comprise a sequence from a gene that may be associated with a disease or a disorder.

In some embodiments the endonuclease recognition site comprises a sequence that is complementary to a sequence that is nicked by an endonuclease. In other embodiments, the sequence that is nicked by the endonuclease is adjacent (downstream or upstream) to the sequence that is specifically recognized by the endonuclease.

In a further aspect, the disclosure relates to a composition for detecting a target nucleic acid in a sample, said composition comprising: an oligonucleotide (sequence conversion DNA or SC DNA) comprising, in the 5' to 3' direction, a signal DNA generation sequence (A), an endonuclease recognition site (B), and a sequence (C) complementary to the 3' end of a target nucleic acid, and which has at least one locked nucleic acid (LNA); a polymerase; and an endonuclease for a nicking reaction.

In a further aspect, the disclosure relates to a composition for detecting a target nucleic acid in a sample, said composition comprising: a first oligonucleotide (sequence conversion DNA or SC DNA) comprising, in the 5' to 3' direction, a signal DNA generation sequence (A), an endonuclease recognition site (B), and a sequence (C) complementary to the 3' end of a target nucleic acid, and which has at least one locked nucleic acid (LNA); a second oligonucleotide (signal amplifier DNA or SA DNA) comprising, in the 5' to 3' direction, a signal DNA generation sequence (D) that is homologous to the signal DNA generation sequence (A) of the first oligonucleotide, an endonuclease recognition site (E) (which may be the same or different from the endonuclease recognition site (B) in the SA DNA), and a sequence (F) that is homologous to the signal DNA generation sequence (A) of the first oligonucleotide, and which has at least one LNA; a polymerase; and an endonuclease for a nicking reaction.

The compositions can also comprise a polymerase, and/or an endonuclease capable of nicking at or adjacent to the endonuclease recognition site of the first and second oligonucleotide when the endonuclease recognition site is double stranded. Compositions can also include other reagents such as reaction buffers, deoxyribonucleotides, and reporter molecules such as, for example, fluorophore-modified probe DNAs (e.g., molecular beacon probes) for the fluorescent detection of newly synthesized DNA.

In yet another aspect, the disclosure relates to a kit for detecting a target nucleic acid in a sample, said kit comprising: an oligonucleotide (sequence conversion DNA or SC DNA) comprising, in the 5' to 3' direction, a signal DNA generation sequence (A), an endonuclease recognition site (B), and a sequence (C) complementary to the 3' end of a target nucleic acid, and which has at least one locked nucleic acid (LNA); a polymerase; and an endonuclease for a nicking reaction. In some embodiments the kits can further comprise a polymerase and/or an endonuclease capable of nicking an endonuclease recognition site or a site adjacent to an endonuclease recognition site. The kits can also include reagents such as reaction buffers, deoxyribonucleotides, and reporter molecules such as, for example, fluorophore-modified probe DNAs (e.g., molecular beacon probes) for the fluorescent detection of newly synthesized DNA such as a signal DNA. The kits can also comprise instructions for use in the practice of any one of the methods disclosed herein.

In yet another aspect, the disclosure relates to a kit for detecting a target nucleic acid in a sample, said kit comprising: a first oligonucleotide (sequence conversion DNA or SC DNA) comprising, in the 5' to 3' direction, a signal DNA generation sequence (A), an endonuclease recognition site (B), and a sequence (C) complementary to the 3' end of a target nucleic acid, and which has at least one locked nucleic acid (LNA); a second oligonucleotide (signal amplifier DNA or SA DNA) comprising, in the 5' to 3' direction, a signal DNA generation sequence (D) that is homologous to the signal DNA generation sequence (A) of the first oligonucleotide, an endonuclease recognition site (E) (which may be the same or different from the endonuclease recognition site (B) in the SA DNA), and a sequence (F) that is homologous to the signal DNA generation sequence (A) of the first oligonucleotide, and which has at least one LNA; a polymerase; and an endonuclease for a nicking reaction. In some embodiments the kits can further comprise a polymerase and/or an endonuclease capable of nicking an endonuclease recognition site or a site adjacent to an endonuclease recognition site. The kits can also include reagents such as reaction buffers, deoxyribonucleotides, and reporter molecules such as, for example, fluorophore-modified probe DNAs (e.g., molecular beacon probes) for the fluorescent detection of newly synthesized DNA such as a signal DNA. The kits can also comprise instructions for use in the practice of any one of the methods disclosed herein.

The methods, oligonucleotides, compositions, and kits disclosed herein may be used in combination with integrated system platforms. For example, methods, oligonucleotides, compositions, and kits of the present invention may be used in combination Abbott's ARCHITECT system. The methods, oligonucleotides, compositions, and kits disclosed herein may be used with sample preparation system platforms such as, for example, the m2000sp sample preparation system (Abbott Diagnostics, Abbott Park, Ill.). Similarly, the methods, oligonucleotides, compositions, and kits disclosed herein may be used with point-of-care system platforms such as, for example, Abbott's i-STAT point-of-care system (Abbott Diagnostics, Abbott Park, Ill.). Further, the methods, oligonucleotides, compositions, and kits of the present invention can be used with any number of other devices, assay platforms, and instrumentation such as, for example, hand held fluorescence detectors, micro-pH meters, microfluidic devices, microarrays, enzymatic detection systems, immunochromatographic strips, and lateral flow devices.

The methods, oligonucleotides, compositions, and kits disclosed herein may be used in the field of molecular diagnostics, including diagnosis of non-infectious and infectious diseases. For example, methods, oligonucleotides, compositions, and kits of the present invention can be used to detect microRNA, messenger RNA, non-coding RNA and methylated DNA in human fluid such as blood, urine, saliva, sweat and feces. Similarly, methods, oligonucleotides, compositions, and kits of the present invention can be used to detect target nucleic acids originating from infectious diseases such as, for example, HBV, HCV, HIV, HPV, HTLV-I, Parvo virus, Tuberculosis, Syphilis, Malaria and *Entamoeba histolytica* in human fluid like blood, urine, saliva, sweat and feces.

It is understood that in some aspects of the present disclosure, the SC and SA DNAs disclosed herein may comprise chemically modified nucleotides other than locked nucleic acids, at the same or different position(s). For example, the SC and SA DNAs disclosed herein may comprise BNA (Bridged Nucleic Acid), ENA (Ethylene Bridged Nucleic Acid), GNA (Glycol Nucleic Acid), TNA (Threose Nucleic Acid), PNA (Peptide Nucleic Acid), Morpholino Nucleic Acid and phosphorothioate nucleotides Additional aspects, embodiments, and advantages provided by the disclosure will become apparent in view of the description that follows.

DETAILED DESCRIPTION

Figure 1A:
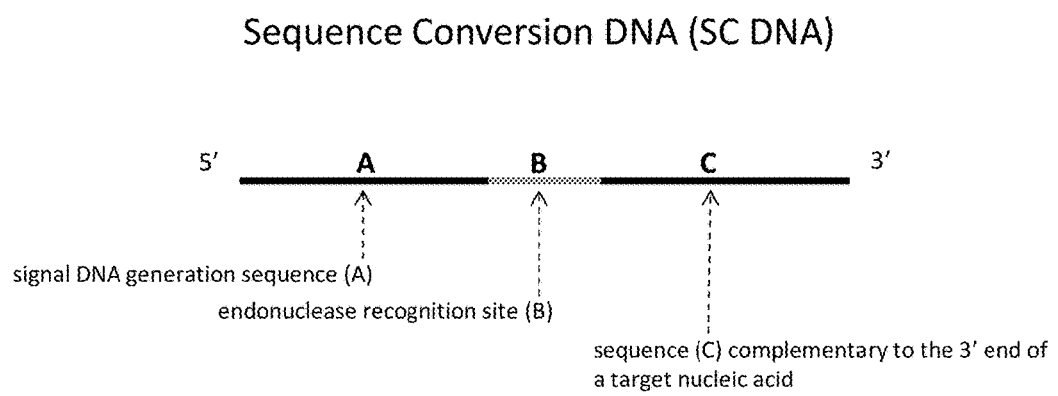
FIG. 1A is a diagram schematically illustrating a non-limiting example of a Sequence Conversion DNA (SC DNA) for the detection of a target nucleic acid in a sample. The SC DNA comprises, in the 5' to 3' direction, a signal generation sequence (A), an endonuclease recognition site (B) that can be used in a nicking reaction, and a sequence (C) complementary to the target nucleic acid and which comprises locked nucleic acid (LNA).

In a general sense, the disclosure relates to nucleic acid constructs that are surprisingly effective in the detection of target nucleic acids in a test sample. The constructs disclosed herein comprise nucleic acid sequences that allow the production of signal DNAs that are generated in the presence of a target nucleic acid, with a concomitant reduction in background signal arising from non-specific amplification events and/or in the absence of a target nucleic acid. The methods and nucleic acid constructs disclosed herein provide for selective and sensitive detection of target nucleic acids that may be advantageously performed under low temperature and isothermal conditions.

In an aspect, the disclosure relates to a chemically modified oligonucleotide, which may be referred to herein as a "signal amplifier DNA" (or "SA DNA") comprising, in the 5' to 3' direction, a first sequence that is complementary to a known signal DNA sequence, an endonuclease recognition site, and a second sequence that is complementary to the same known signal DNA sequence as the first sequence, wherein the second sequence comprises a locked nucleic acid (LNA). The first sequence is the signal DNA generation sequence (D) in FIG. 1B, that is homologous to a known signal DNA generation sequence (A) of a SC DNA. The second sequence is sequence (F) in FIG. 1B, that is homologous to the same known signal DNA generation sequence (A) of the same SC DNA, and which has at least one LNA. In some embodiments of this aspect, the second sequence comprises a plurality of LNAs (e.g., 2, 3, 4, 5, 6, 7, 8, 9, or 10 LNAs). In some embodiments, the second sequence comprises from 2-6 LNAs. In some embodiments, the second sequence comprises 2 LNAs, 3 LNAs, or 4 LNAs. In other embodiments the chemically modified oligonucleotide further comprises a 3'-end modification.

In this aspect, the lengths of the first and second sequences may vary, but typically each of the sequences is about the same length as the other. In embodiments, the length of the sequences may be in a range from about 5 to about 100 nucleotides, but are more typically from about 5 to about 30, from about 10 to about 30, or from about 15 to about 30 nucleotides in length. The endonuclease recognition site comprises a sequence that can be recognized, bound, and nicked by an endonuclease as described herein. Such sequences are generally known in the art. The endonuclease recognition site can comprise additional nucleotides either 5' or 3' to the endonuclease binding site (or both 5' and 3') but is typically no more than 10 nucleotides in length.

In certain embodiments described herein, the location of the LNA, or the plurality of LNAs, in the second sequence are identified with respect to the 3'-end of the sequence and may vary. In some embodiments the LNA or the plurality of LNAs is located at position(s) 1, 2, 3, 4, 5, 6, 7, 8, 9, 10, 11, 12, 13, 14, 15, 16, 17, 18, 19, or 20 from the 3'-end of the sequence. In some embodiments that comprise a single LNA, the LNA is located at any of positions 1, 4, 5, 6, 7, 8, 9, 10, 11, 12, 13, 14, 15, 16, 17, 18, 19, or 20 from the 3'-end of the sequence.

In embodiments that comprise two LNAs, the LNAs may be located at any combination of two positions selected from positions 1 to 20 from the 3'-end of the sequence. In some embodiments, the LNAs may be located at position 6 and at any other positions 1-5 and 7-20 (e.g., 1 and 6, 2 and 6, 3 and 6, 4 and 6, 5 and 6, 7 and 6, 8 and 6, 9 and 6, 10 and 6, 11 and 6, 12 and 6, 13 and 6, 14 and 6, 15 and 6, 16 and 6, 17 and 6, 18 and 6, 19 and 6, or 20 and 6) from the 3'-end of the sequence; at positions 1 and 2; at positions 1 and 10; at positions 2 and 10; at positions 4 and 8; at positions 5 and 9; at positions 1 and 8; at positions 2 and 8; at positions 3 and 8; and at positions 2 and 7 from the 3'-end of the sequence.

In embodiments that comprise three LNAs, the LNAs may be located at any combination of three positions selected from positions 1 to 20 from the 3'-end of the sequence. In some embodiments the LNAs may be located at position 6 and at any other combination of two positions 1-5 and 7-20 from the 3'-end of the sequence; and at positions 1, 2, and 10 from the 3'-end of the sequence.

In embodiments that comprise four LNAs the LNAs may be located at any combination of four positions selected from positions 1 to 20 from the 3'-end of the sequence. In some embodiments the LNAs may be located at position 6 and at any other combination of three positions 1-5 and 7-20 from the 3'-end of the sequence.

In embodiments of this aspect, the disclosure provides novel Sequence Conversion (SC) and Signal Amplifier (SA) oligonucleotide constructs, and combinations thereof, that are useful in detecting a target nucleic acid in a sample, with a concomitant reduction in background signal. As depicted by the illustrative embodiment of FIG. 1A, a Sequence Conversion DNA (SC DNA) oligonucleotide for the detection of a target nucleic acid in a sample comprises, in the 5' to 3' direction, a signal DNA generation sequence (A), an endonuclease recognition site (B), and a sequence (C) complementary to the 3' end of a target nucleic acid, and which has at least one locked nucleic acid (LNA).

Figure 1B:
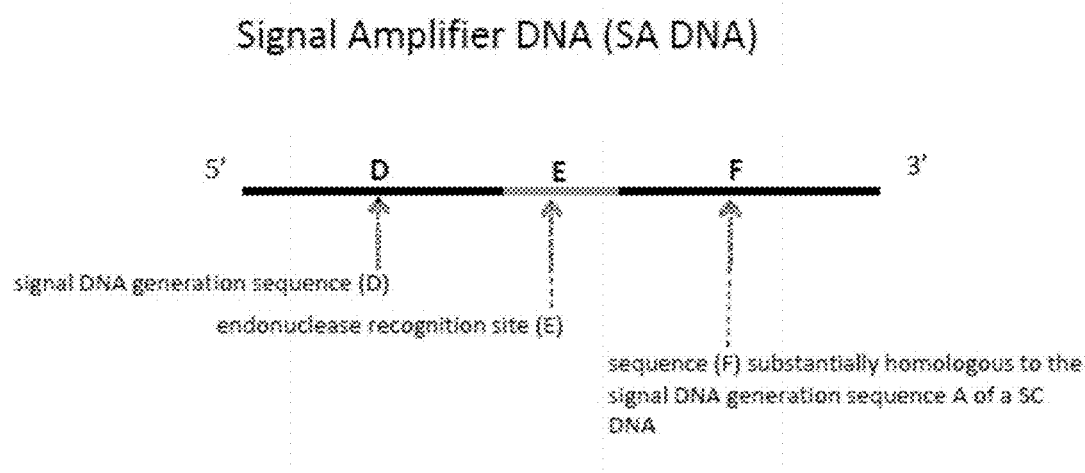
FIG. 1B is a diagram schematically illustrating a non-limiting example of a Signal Amplifier DNA (SA DNA) for the detection of a target nucleic acid in a sample. The SA DNA comprises, in the 5' to 3' direction, a signal DNA generation sequence (D) homologous to the signal DNA generation sequence (A) of a SC DNA; an endonuclease recognition site (E) (which may be the same or different from the endonuclease recognition site (B) of a SC DNA), and a sequence (F) that is homologous to the signal DNA generation sequence (A) of a first SC DNA, and which comprises locked nucleic acid.

As depicted by the illustrative embodiment of FIG. 1B, a Signal Amplifier DNA (SA DNA) for the detection of a target nucleic acid in a sample comprises, in the 5' to 3' direction, a signal DNA generation sequence (D) homologous to the signal DNA generation sequence (A) of a SC DNA; an endonuclease recognition site (E) (which may be the same or different from an endonuclease recognition site (B) of a SC DNA), and a sequence (F) comprising a locked nucleic acid (LNA) and a sequence that is homologous to the signal DNA generation sequence (A) of a SC DNA.

In some embodiments of the present disclosure, both sequence (C) of the SC DNA and sequence (F) of the SA DNA comprise locked nucleic acids (LNA). In other embodiments, only sequence (F) of the SA DNA will comprise locked nucleic acids (LNA). A locked nucleic acid is a modified RNA nucleotide having the following structure:

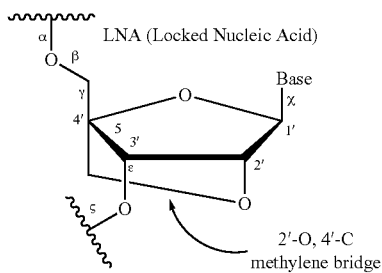

As illustrated, the ribose moiety of an LNA nucleotide is modified from a typical ribose ring structure by a methylene bridge that connects the 2' oxygen atom and the 4' carbon atom, and which locks the ribose in the 3'endo conformation. Such LNAs can comprise any natural purine or pyrimidine base or non-natural bases (e.g., inosine, chemically modified bases, etc.).

By incorporating LNAs into an amplification oligonucleotide such as, for example, sequence (F) of the SA DNA described herein, or into sequence (C) of the SC DNA, non-specific background signal amplification is either eliminated entirely or delayed for a period of time that is adequate to detect signal sequence resulting from the presence of target nucleic acid without any interference from non-specific background signal. For example, in some embodiments a signal resulting from the presence of from about 1 nM to about 1 fM target nucleic acid in a sample is detectable within about 5 to about 120 minutes, within about 5 to about 90 minutes, within about 5 to about 60 minutes, within about 5 to about 30 minutes, or within about 5 to about 15 minutes before any non-specific background signal is detectable. In some embodiments a signal resulting from the presence of from about 1 nM to about 1 pM target nucleic acid in a sample is detectable within about 5 to about 120 minutes, within about 5 to about 90 minutes, within about 5 to about 60 minutes, within about 5 to about 30 minutes, or within about 5 to about 15 minutes before any non-specific background signal is detectable. In other embodiments a signal resulting from the presence of from about 1 pM to about 1 fM target nucleic acid in a sample is detectable within about 5 to about 120 minutes, within about 5 to about 90 minutes, within about 5 to about 60 minutes, within about 5 to about 30 minutes, or within about 5 to about 15 minutes before any non-specific background signal is detectable. In some embodiments, the method does not generate any detectable non-specific background signal.

As described above, LNAs are incorporated into sequence (F) of the SA DNA, and into sequence (C) of the SC DNA, at any position effective to reduce or eliminate non-specific background signal amplification in the absence of target nucleic acid. In some embodiments, LNAs are incorporated into sequence (F) of the SA DNA, and into sequence (C) of the SC DNA, at position 1, 2, 3, 4, 5, 6, 7, 8, 9, 10, 11, 12, 13, 14, 15, 16, 17, 18, 19, 20 or combinations thereof, from the 3' end the respective SC or SA DNA. In some embodiments, an LNA is located at position 6, or positions 3 and 6, from the 3' end of the SA DNA. In other embodiments, LNAs are present in the SA DNA at positions (counting from the 3' end): 1, 2, 6, and 10 (e.g., SEQ ID NO.: 2); 1, 2, and 6 (e.g., SEQ ID NO.: 3); 1, 2, and 10 (e.g., SEQ ID NO.: 4); 1, 6, and 10 (e.g., SEQ ID NO.: 5); 2, 6, and 10 (e.g., SEQ ID NO.: 6); 1 and 2 (e.g., SEQ ID NO.: 7); 1 and 6 (e.g., SEQ ID NO.: 8); 2 and 6 (e.g., SEQ ID NO.: 9); 1 and 10 (e.g., SEQ ID NO.: 10); 2 and 10 (e.g., SEQ ID NO.: 11); 1 (e.g., SEQ ID NO.: 16); 4, and 8 (e.g., SEQ ID NO.: 23); 2, 3, and 6 (e.g., SEQ ID NO.: 26); 2, 3, 6, and 10 (e.g., SEQ ID NO.: 27); or 3 and 10 (e.g., SEQ ID NO.: 35).

Figure 3:
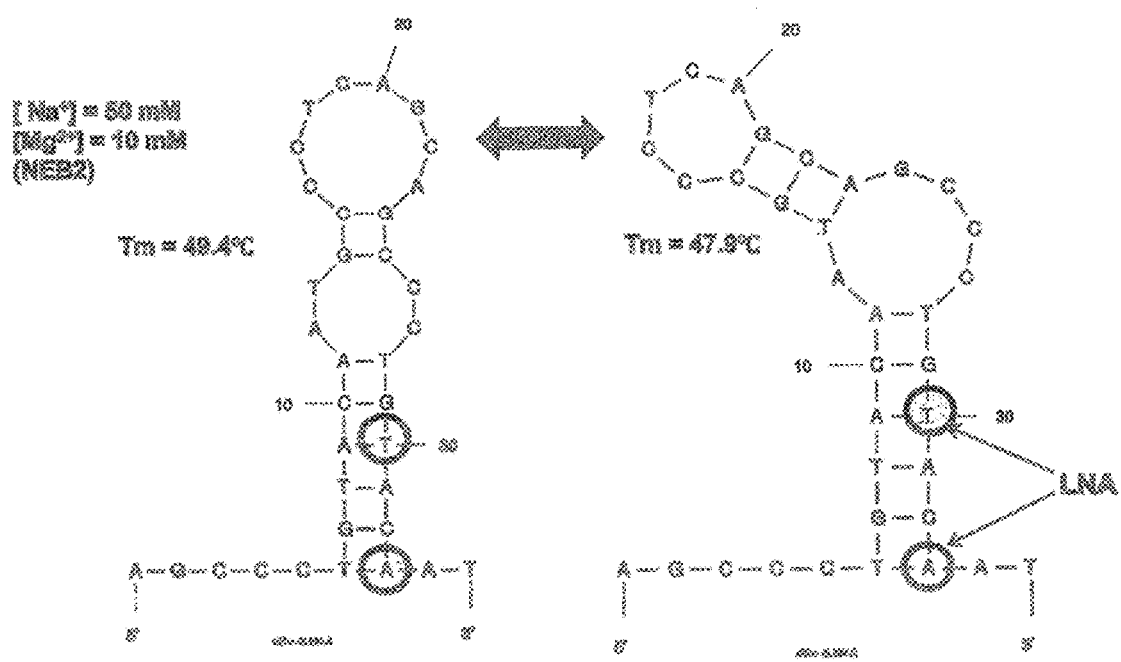
FIG. 3 depicts the predicted hairpin structure of SA DNA #339 (SEQ ID NO.: 25) calculated using DINAMelt (*Nucleic Acids Res.*, 33, W577-W581; and *Bioinformatics: Structure, Function and Applications* (Series: Methods in Molecular Biology, Vol. No.: 453), chapter 1, pages 3-31 (ISBN 978-1-60327-428-9)). Also shown is the location of two LNAs within the stem of the hairpin structure at positions 3 and 6 from the 3' end of SA DNA #339.

In some embodiments, LNA(s) are incorporated into sequence (F) of the SA DNA, and into sequence (C) of the SC DNA, at or within a particular structural motif incorporating either sequence. For example, the sequence (F) of the SA DNA can form a hairpin (stem-loop) structure with itself or with portions of some other sequence within the SA DNA (e.g., sequence (D) or (E)), and the LNA may be located within the stem. The stem may comprise from between about 2 to about 10 base pairs, from between about 2 to about 8 base pairs, from between about 2 to about 6 base pairs, or from between about 2 to about 4 base pairs, and all integers between 2 and 10 base pairs. Alternatively, the LNA can be located in a single stranded DNA region (e.g., a loop or 3' tail end of a hairpin structure). Likewise, the sequence (C) of the SC DNA can form a hairpin (stem-loop) structure with itself or with portions of some other sequence within the SC DNA (e.g., sequence (A) or (B)), and the LNA may be located within the stem. In the alternative, the LNA can be located in a single stranded DNA region (e.g., a loop or 3' tail end of a hairpin structure). (See, e.g., FIG. 3.)

As illustrated in FIG. 1A, the SC DNAs disclosed herein comprise a signal generation sequence (A). The signal generation sequence (A) in the SC DNA can comprise any desired nucleic acid sequence and is not limited by any particular sequence. As discussed in greater detail below, the signal generation sequence (A) provides at least a portion of the template for a signal DNA (e.g., nucleic acid (S) in FIG. 2), the production of which indicates the presence of target nucleic acid. The signal generation sequence (A) in the SC DNA is not limited by length. In some embodiments, the signal generation sequence (A) in the SC DNA is from about 5 to about 100 nucleic acid bases, and all integers between 5 and 100. In embodiments, the signal generation sequence (A) in the SC DNA is from about 5 to about 30 nucleic acid bases, and all integers between 5 and 30. In some embodiments, the signal generation sequence (A) in the SC DNA is from about 10 to about 30 nucleic acid bases, and all integers between 10 and 30. In yet further embodiments, the signal generation sequence (A) in the SC DNA is from about 15 to about 30 nucleic acid bases, and all integers between 15 and 30 (e.g., about 16, about 17, about 18, about 19, about 20, about 21, about 22, about 23, about 24, about 25, about 26, about 27, about 28, about 29 or about 30 bases).

As illustrated in FIG. 1B, the SA DNAs disclosed herein comprise a signal DNA generation sequence (D) which is homologous to the signal DNA generation sequence (A) of a SC DNA, and a sequence (F) (comprising a locked nucleic acid) which is homologous to the same signal DNA generation sequence (A) of the same SC DNA. In some embodiments, in order to be homologous to the signal DNA generation sequence (A) of a SC DNA, sequences (D) and (F) are completely identical to the corresponding signal DNA generation sequence (A). In other embodiments, sequence (F) is identical in sequence to the corresponding signal DNA generation sequence (A) of a SC DNA, except that it is from about 1 to about 5, or from about 1 to about 4, or from about 1 to about 3, or from about 1 to about 2, or 1 base(s) shorter at the 3' end. When the signal DNA generation sequence (D) of a SA DNA is homologous to the signal DNA generation sequence (A) of a SC DNA, it follows that the same signal DNA (S) is produced and exponentially amplified.

Figure 2A:
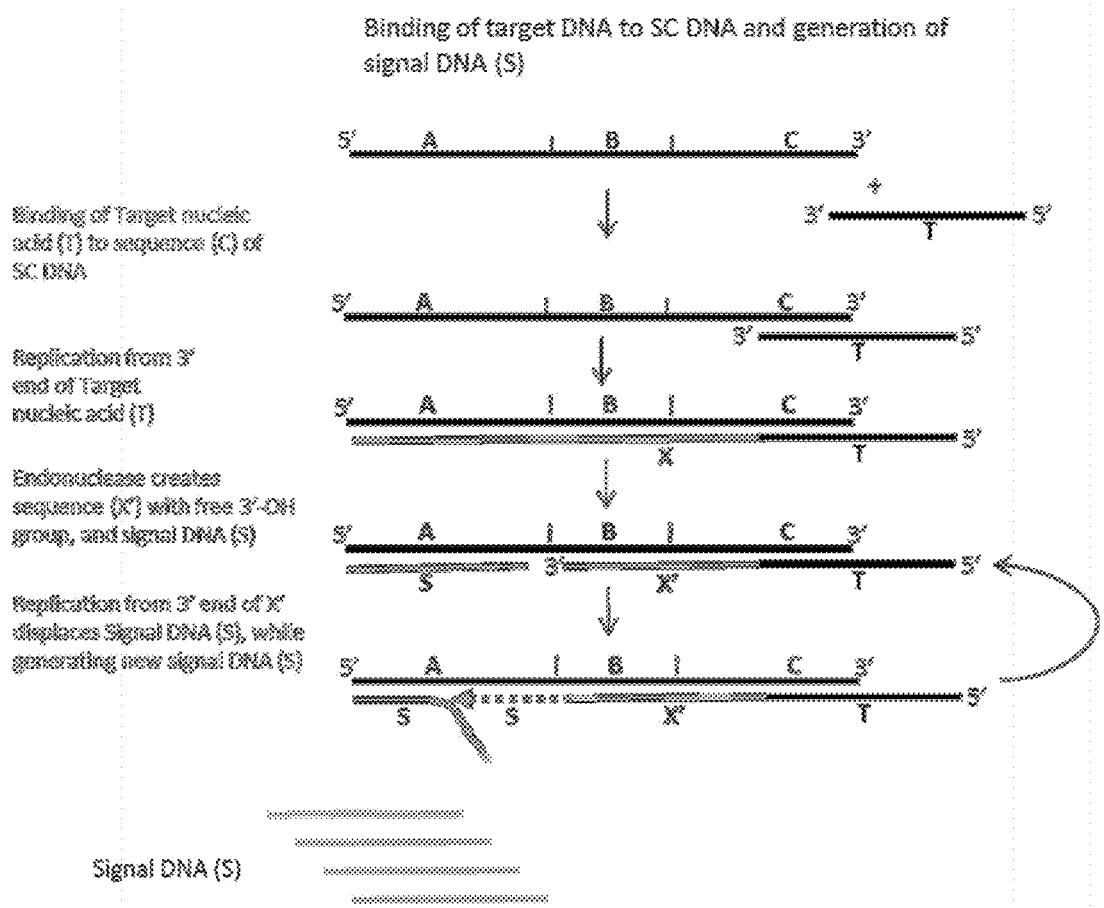
FIG. 2A is a diagram schematically illustrating the progression of an exemplary reaction of a target (T) nucleic acid with a Sequence Conversion (SC) DNA for the detection of a target nucleic acid in a sample. Sequences (A)-(C) are as described in FIG. 1A, sequence (T) represents a target sequence, sequence (X) represents the sequence produced when Target (T) bound to sequence (C) is extended by polymerase, sequence (X') represents the nicked extension sequence, and sequence (S) represents the signal DNA sequence eventually produced.

The SC and SA DNAs comprise endonuclease recognition sites (B) and (E) respectively, which can be the same or different. In single stranded form (e.g., the structure of FIGS. 1A and 1B) the endonuclease recognition sites (B) and (E) may comprise a sequence that is complementary to a sequence that may be nicked by an endonuclease. The sequence that is nicked by the endonuclease may be within, downstream, or upstream from the sequence that is recognized by the endonuclease. Suitably, when double stranded, the endonuclease recognition sites (B) and (E) can be recognized by one or more endonucleases present in the reaction, and the endonuclease recognition sites (B) and (E) (or a sequence adjacent to the endonuclease recognition sites (B) and (E)) may be cleaved on only one strand of the double-stranded DNA (i.e., nicked). As described in greater detail below, binding of a target nucleic acid to the complementary sequence (C) of the SC DNA primes replication via DNA polymerase to create an active, double-stranded form of the endonuclease recognition site (B) that can now serve as a recognition site for an endonuclease (FIG. 2A). Endonuclease nicking at the newly created double-stranded endonuclease site (B), or at a site adjacent to newly created double-stranded endonuclease site (B), then primes replication via DNA polymerase and generates signal DNA (S) (see, e.g., FIG. 2A). As illustrated in FIG. 2A, the endonuclease recognition site (B) is oriented such that the newly replicated strand is nicked, not the SC DNA. That is, when the newly replicated strand is generated the orientation of the endonuclease recognition site in (B) directs endonuclease activity (cleavage) of the newly replicated strand. As such, the endonuclease recognition site comprises a sequence that is complementary to a sequence that is nicked by an endonuclease, allowing the SC oligonucleotide to remain intact throughout the reaction (i.e., the SC DNA is not nicked or cleaved).

Figure 2B:
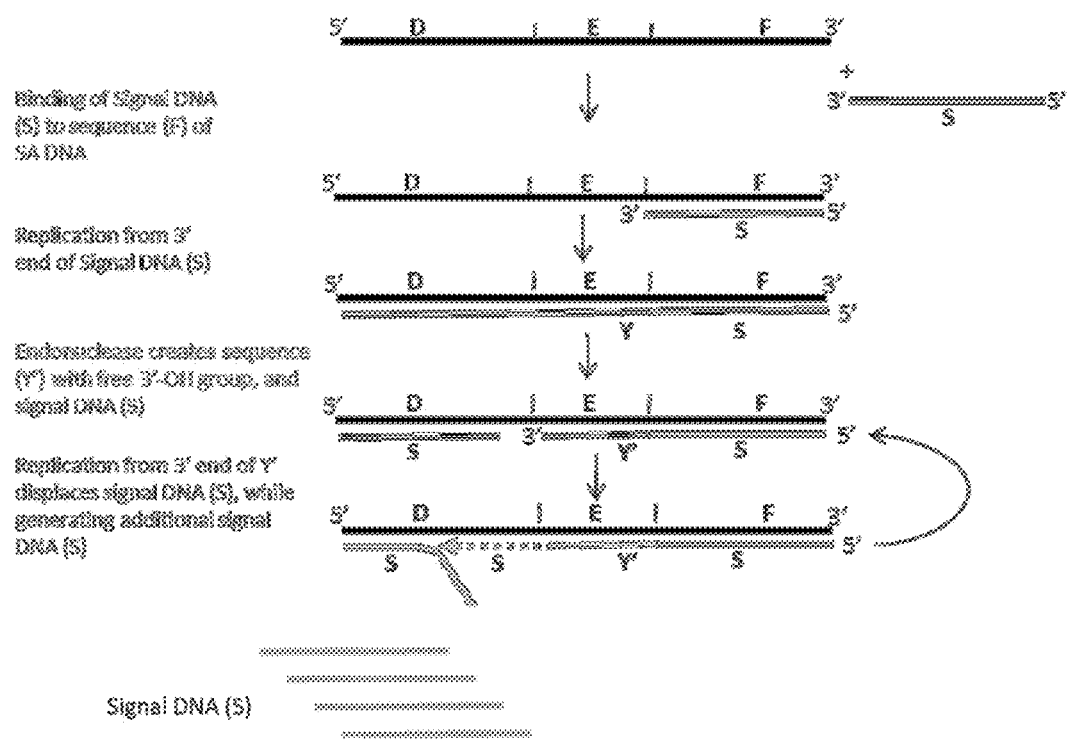
FIG. 2B is a diagram schematically illustrating the progression of an exemplary reaction of a signal DNA (S) with a Signal Amplification (SA) DNA for the detection of a target nucleic acid in a sample. Sequences (D)-(F) are as described in FIG. 1B, sequence (S) is the Signal DNA produced from reaction of Target (T) nucleic acid with SC DNA as described in FIG. 2A, sequence (Y) represents the sequence produced when Signal DNA (S) bound to sequence (D) is extended by polymerase, sequence (Y') represents the nicked extension sequence, and sequence (S) represents the signal DNA sequence eventually produced. Because the SA signal generation sequence (D) is homologous to the SC signal generation sequence (A), the same signal DNA (S) is produced.

As described in greater detail below, binding of signal DNA (S), generated from the signal generation sequence (A) of a SC DNA, to the sequence (F) of a SA DNA primes replication via DNA polymerase to create an active, double-stranded form of the endonuclease recognition site (E) of the SA DNA that can serve as a recognition site for an endonuclease (FIG. 2B). Endonuclease nicking at the newly created double-stranded endonuclease site (E) of the SA DNA, or at a site adjacent to newly created double-stranded endonuclease site (E), then primes replication via DNA polymerase and generates signal DNA (S) that is the same as signal DNA (S) generated from the SC DNA (FIG. 2B). As illustrated in FIG. 2B, the endonuclease recognition site (E) is oriented such that the newly replicated strand is nicked, not the SA DNA. That is, when the newly replicated strand is generated the orientation of the endonuclease recognition site in E directs endonuclease activity (cleavage) of the newly replicated strand. As such, the endonuclease recognition site comprises a sequence that is complementary to a sequence that is nicked by an endonuclease, allowing the SA oligonucleotide to remain intact throughout the reaction (i.e., the SA DNA is not nicked or cleaved).

The sequence (C) of the SC DNA that is complementary to the target DNA is not limited by length, and can be from about 5 to about 100 nucleic acid bases, and all integers between 5 and 100. In some embodiments, the sequence (C) of the SC DNA is from about 5 to about 30 nucleic acid bases, and all integers between 5 and 30. In some embodiments, the sequence (C) in the SC DNA is from about 10 to about 30 nucleic acid bases, and all integers between 10 and 30. In further embodiments, the sequence (C) of the SC DNA is from about 15 to about 30 nucleic acid bases, and all integers between 15 and 30.

Complementary sequences are capable of forming hydrogen bonding interactions to form a double stranded nucleic acid structure (e.g., nucleic acid base pairs). For example, a sequence that is complementary to a first sequence includes a sequence which is capable of forming Watson-Crick base-pairs with the first sequence. As used herein, the term "complementary" does not require that a sequence is complementary over the full-length of its complementary strand, and encompasses a sequence that is complementary to a portion of another sequence. Thus, in some embodiments, a complementary sequence encompasses sequences that are complementary over the entire length of the sequence or over a portion thereof (e.g., greater than about 10%, about 20%, about 30%, about 40%, about 50%, about 60%, about 70%, about 80%, or about 90% of the length of the sequence). For example, two sequences can be complementary to each other over a length ranging from about 2 to about 100 consecutive (contiguous) nucleotides, or any integer between 2 and 100. In some embodiments, two sequences can be complementary to each other over a length ranging from about 15 to about 30 consecutive (contiguous) nucleotides, or any integer between 15 and 30. As used herein, complementary sequences can encompass sequences that have some sequence mismatches. For example, complementary sequences can include sequences that are complementary to at least about 70% to 100%, preferably greater than above 95% of the length of the sequence. Despite some amount of mismatches, complementary sequences generally have the ability to selectively hybridize to one another under appropriate conditions such as, for example, stringent and highly stringent conditions such as those described herein or generally known by those of ordinary skill in the art.

The SC and SA DNAs may be synthesized by known methods. For example, the SC and SA DNAs can be synthesized using a phosphoramidite method, a phosphotriester method, an H-phosphonate method, or a thiophosphonate method. In some embodiments, the SC and/or SA DNAs can be purified, for example using ion exchange HPLC.

The SC and SA DNAs may comprise chemical modifications such as are generally known in the art. In some embodiments, for example, the SC and SA DNAs can comprise chemically modified nucleotides (e.g., 2'-0 methyl derivative, phosphorothioates, etc.), 3' end modifications, 5' end modifications, or any combinations thereof. In some embodiments, the 3' end of the SC and SA DNAs may be modified such that an extension reaction does not occur from the 3' end of the SC or SA DNA (e.g., upon binding of a target sequence, or another non-target sequence, that might serve as a primer for polymerase extension). As illustrated in FIG. 2A, it is the 3' end of the target nucleic acid (T), not the SC DNA, which initiates DNA replication. Any replication initiated from the 3' end of the SC or SA DNAs may lead to detection errors (e.g., false positives). Further, non-specific extension reactions from an unmodified 3' end of the SC DNA arising from events such as, for example, binding between the SC DNA and a non-target sequence, binding between the SC DNA and a target sequence at an incorrect position, binding between SC and SA DNAs, or non-templated de novo or ab initio DNA synthesis may also lead to detection errors. Accordingly, in embodiments, the SC and SA DNAs comprise a 3' end modification that can reduce or eliminate the occurrence of any non-desired extension reactions, such as those discussed above. Non-limiting examples of 3'-end modifications include TAMRA, DABCYL, and FAM. Other non-limiting examples of modifications include, for example, biotinylation, fluorochromation, phosphorylation, thiolation, amination, inverted nucleotides, or abasic groups.

In another aspect, the present invention encompasses methods for detecting a target nucleic acid (T) in a sample. The methods generally comprise contacting said sample with: a first oligonucleotide (or sequence conversion DNA or SC DNA) comprising, in the 5' to 3' direction, a signal DNA generation sequence (A), an endonuclease recognition site (B), and a sequence (C) having a locked nucleic acid (LNA) and which is complementary to the 3' end of said target nucleic acid (T); a second oligonucleotide (or signal amplifier DNA or SA DNA) comprising, in the 5' to 3' direction, a signal DNA generation sequence (D) homologous to the signal DNA generation sequence (A) of the first oligonucleotide, an endonuclease recognition site (E) (which is the same as the endonuclease recognition site (B) of the first oligonucleotide), and a sequence (F) comprising a locked nucleic acid (LNA) and which is homologous to the signal DNA generation sequence (A) of the first oligonucleotide; a polymerase; and an endonuclease for a nicking reaction. In embodiments of this aspect, the method also comprises determining the presence or absence of a signal DNA, wherein the presence of the signal DNA indicates the presence of the target nucleic acid in the sample.

The method comprises contacting a sample with an endonuclease. The endonuclease may be a nicking endonuclease or a restriction endonuclease that is capable of or that can be used in nicking the sequence complementary to the endonuclease recognition site (B) within the SC DNA, or the sequence complementary to the endonuclease recognition site (E) within the SA DNA. In some embodiments, the endonuclease comprises a nicking endonuclease or a restriction endonuclease that can catalyze or can be used to catalyze a double-stranded DNA nicking reaction. In embodiments providing a nicking endonuclease, the phosphodiester linkage of one strand of a double-strand DNA may be cleaved to generate a phosphate group on the 5' side of the cleavage site and a hydroxyl group on the 3' side. Non-limiting examples of nicking endonucleases include Nb.BbvCI, Nt.AlwI, Nt.BbvCI, Nb.BsrDI, Nb.BtsI, Nt.BspQI, Nt.BstNBI, Nb.BsmI, Nt.CviPII, and Nt.BsmAI.

In some embodiments, the endonuclease may be a restriction endonuclease. In these embodiments the restriction endonuclease recognition site may be modified so that the restriction endonuclease cleaves the phophodiester bond on only one strand of a double stranded DNA, and generates a nick in the double strand. Methods or strategies may be used to modify the activity of the restriction endonuclease such as, for example, including a chemical modification in at least one strand of a double-stranded nucleic acid that is not cleaved by the restriction enzyme. One non-limiting example of such a modification includes replacing the oxygen atom of phosphodiester linkage of one strand with a sulfur atom.

In embodiments providing a restriction endonuclease, the phosphodiester linkage of one strand of a double-strand DNA may be cleaved to generate a phosphate group on the 5' side of the cleavage site and a hydroxyl group on the 3' side. Non-limiting examples of restriction endonucleases include Hinc II, Hind II, Ava I, Fnu4HI, Tth111I and NciI.

The method comprises contacting a sample with a polymerase. In some embodiments, the polymerase may be a DNA polymerase having strand displacement activity. In some embodiments, the polymerase may be a polymerase that lacks 5'-3' exonuclease activity, lacks 3'-5' exonuclease activity, or lacks both 5'-3' and 3'-5' exonuclease activity. The polymerase may be eukaryotic, prokaryotic, or viral in origin, and can also be genetically modified. In some embodiments, the polymerase is selected from among those that function at lower temperatures, including ambient (e.g., room) temperatures. Non-limiting examples of DNA polymerases include Klenow fragments, DNA polymerase I derived from *E. coli*, 5' to 3' exonuclease-deficient Bst DNA polymerases derived from *Bacillus stearothermophilus*, and 5' to 3' exonuclease-deficient Bca DNA polymerases derived from *Bacillus caldotenax*.

One non-limiting embodiment of the methods disclosed herein is illustrated in FIGS. 2A and 2B. Briefly, as illustrated in FIG. 2A, a sample is contacted with SC DNA in the presence of a DNA polymerase and an endonuclease capable of nicking the double-stranded form (i.e., complementary sequence) of the endonuclease recognition site (B), or a site adjacent to the double-stranded form of the endonuclease recognition site (B). If a target nucleic acid (T) is present in the sample, the 3' end sequence of the target nucleic acid (T) hybridizes to the sequence (C) of the SC DNA which is complementary to the target and primes or initiates replication (by the DNA polymerase present in the reaction mixture) thereby generating double stranded extension sequence (X) that includes the double stranded endonuclease recognition site (B). Recognition of the newly-generated double stranded endonuclease recognition site (B) (by the endonuclease present in the reaction mixture), and subsequent nicking of the newly-generated strand (by the endonuclease present in the reaction mixture), generates oligonucleotide signal sequence (S) and extension sequence (X'). Because the 3'-OH of sequence (X') at the nick serves as an initiation site for subsequent rounds of strand displacement replication, oligonucleotide (S) is displaced from the SC DNA by DNA polymerase which continues to replicate and amplify signal DNA (S) in the reaction mixture.

As further illustrated in FIG. 2B, the signal resulting from the production of signal DNA (S) can be further amplified by the presence of a signal amplifier DNA (or SA DNA). Briefly, signal DNA (S) present in a reaction hybridizes to the sequence (F) of the SA DNA which primes or initiates replication (by the DNA polymerase present in the reaction mixture) thereby generating double stranded extension sequence (Y) that includes the double stranded endonuclease recognition site (E). Recognition of the newly-generated double stranded endonuclease recognition site (E) (by endonuclease present in the reaction mixture), and subsequent nicking of the newly-generated strand (by endonuclease present in the reaction mixture), generates oligonucleotide signal sequence (S) and extension sequence (Y'). Because the 3'-OH of sequence (Y') at the nick serves as an initiation site for subsequent rounds of strand displacement replication, oligonucleotide (S) is displaced from the SA DNA by DNA polymerase which continues to replicate and amplify signal DNA (S) in the reaction mixture.

Methods according to the invention may be performed under isothermal or substantially constant temperature conditions. In embodiments that relate to performing the method under a substantially constant temperature, some fluctuation in temperature is permitted. For example, in some embodiments a substantially constant temperature may fluctuate within a desired or identified target temperature range (e.g., about +/−2° C. or about +/−5° C.). In some embodiments, a substantially constant temperature may include temperatures that do not include thermal cycling. In some embodiments, methods can be performed at isothermal or substantially constant temperatures such as, for example, (1) temperatures at or below about the calculated/predicted or experimentally determined optimal hybridization or annealing temperature of the target nucleic acid (T) to sequence (C) of the SC DNA; (2) temperatures at or below the melting temperature of the target nucleic acid (T) bound to SC DNA (typically, hybridization or annealing temperatures are slightly below the melting temperature); (3) temperatures at or below the melting temperature of the signal DNA (S) bound to SA DNA; or (4) temperatures at or about the calculated/predicted or experimentally determined optimal reaction temperature for the polymerase and/or endonuclease present in the reaction mixture.

The methods may comprise reaction temperatures that range from about 20° C. to about 70° C., including lower temperatures falling within the range of about 20° C. to about 42° C. In some embodiments, the reaction temperature range is from 35° C. to 40° C. (e.g., 35° C., 36° C., 37° C., 38° C., 39° C., or 40° C.). In other embodiments, the reaction temperature is below 65° C., including lower temperatures below about 55° C., about 50° C., about 45° C., about 40° C., or about 30° C. In still other embodiments, reaction temperatures may be about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., or about 70° C.

The methods may be performed for a time that is adequate to allow for amplification of a detectable amount of signal sequence in the presence of a target nucleic acid. In some embodiments, the reaction time may range from about 5 minutes to 16 hours, or from about 3 minutes to 16 hours. In still other embodiments, the reaction time may range from about 5 to 120 minutes, or from about 15 to 60 minutes.

Throughout the specification, oligonucleotide (S) is also referred to as a signal DNA (S). Because signal DNA is generated only in the presence of the target nucleic acid (T), methods according to the present invention detect the presence or absence of a target nucleic acid (T) in a sample by detecting the presence or absence of signal DNA. The signal DNA (S) is not limited by sequence, and can be any sequence that is amenable to detection. The signal DNA is also not limited by length. Preferably, the signal DNA can be from about 5 to about 100 bases, and any integer between 5 and 100. In some embodiments, the signal DNA can be from about 5 to about 30 nucleic acid bases, and all integers between 5 and 30. In some embodiments, the signal DNA can be from about 10 to about 30 bases in length and all integers between 10 and 30. In yet further embodiments, the signal DNA can be from about 15 to about 30 bases in length and all integers between 15 and 30.

Methods according to the disclosure may be performed under buffer conditions that comprise a pH range from about 4 to about 10, or from about 7 to about 9. The buffer may comprise a salt concentration from about 10 mM to about 500 mM, or from about 50 mM to 150 mM. In some embodiments the method may be performed using an amount of SC and/or SA DNAs that allows for amplification of a detectable amount of signal sequence in the presence of a target nucleic acid. In some embodiments, the SC and/or SA DNA concentration may range from about 100 pM to about 100 µM, from about 1 nM to about 150 nM, from about 5 nM to about 50 nM, or from about 5 nM to about 25 nM.

The presence of signal DNA (S) can be detected by any method known in the art. For example, gel electrophoresis and staining with ethidium bromide can be used. Also, the presence of signal DNA can be detected using fluorescence polarization, immunoassay, fluorescence resonance energy transfer, enzyme labeling (such as peroxidase or alkaline phosphatase), fluorescent labeling (such as fluorescein or rhodamine), chemiluminescence, bioluminescence, surface plasmon resonance (SPR), or a fluorophore-modified probe DNA (e.g., TaqMan probe). The amplification product can also be detected by using a labeled nucleotide labeled with a biotin, for example. In such a case, the biotin in the amplification product can be detected using fluorescence-labeled avidin or enzyme-labeled avidin, for example. The amplification product can also be detected with electrodes by using redox intercalator known to those skilled in the art. The amplification product can also be detected using surface plasmon resonance (SPR), a Quarts Crystal Microbalance (QCM), or electrochemical methods (including those methods employing nanopore sensors).

The methods according to the present invention detect the presence or absence of a target nucleic acid (T) in a sample. The methods according to the present invention can also be used to quantitatively measure the concentration of a target nucleic acid in a test sample. For example, methods according to the present disclosure can be performed in the presence of a range of different known concentrations of the target nucleic acid, and calibration curves can then be prepared and used as generally practiced in the art. The target nucleic acid ((T) in FIG. 2) can comprise any nucleic acid sequence and can include DNA, RNA, chemically modified nucleic acids, non-natural nucleic acids, nucleic acid analogs, or any hybrid or combination thereof. Accordingly, in some embodiments, DNA may include cDNA, genomic DNA, and synthetic DNA, and RNA may include total RNA, mRNA, rRNA, siRNA, hnRNA, piRNA, aRNA, miRNA, and synthetic RNA. While some embodiments relate to particular target nucleic acid sequences, any nucleic acid sequence, including auxiliary nucleic acid sequence, can be a target nucleic acid sequence to be detected. The disclosure provides for the detection of a target nucleic acid with selectivity and sensitivity even when the nucleic acid is a short-chain nucleic acid. Accordingly, the degree of complementarity between sequences (C) of the SC DNA and target nucleic acid (T) allows for specific hybridization between the sequences (e.g., the number of complementary nucleotides in sequence (C) of the sequence conversion DNA and target nucleic acid (T) sequences avoids non-specific hybridization under a given set of reaction conditions).

In embodiments, the target nucleic acid sequence can be from, or derived from any number of sources including, for example, genomic DNA, expressed mRNA, nucleic acid sequences from pathogens (microbes, viruses), or therapeutic nucleic acids. Accordingly, the SC and SA DNAs and the methods disclosed herein may be used for the diagnosis and prognosis of diseases (e.g., arising from genetic and infectious sources), identification of contaminants (e.g., foodborne illnesses, equipment contamination), personalized medicine (e.g., monitoring and/or prognosis of a therapy), and the like. For example, molecular diagnostic testing can be performed with respect to the following infectious diseases: Hepatitis B Virus (HBV); hepatitis C (HCV); HCV (genotypes 1-6); Human Immunodeficiency Virus type 1 (HIV-1); Chlamydia trachomatis; Neisseria gonorrhoeae; influenza A; influenza B; Respiratory Syncytial Virus (RSV); and Parvo virus.

In some embodiments, the target nucleic acid can comprise micro-RNAs (miRNA). Micro-RNAs include small non-coding RNA molecules of about 22 nucleotides. Micro-RNAs are known to function in transcription and post-transcriptional regulation of gene expression. It is known that micro-RNAs function by base pairing with complementary regions of messenger RNA (mRNA), resulting in gene silencing via translational repression or target degradation.

Any type of sample that may comprise a target nucleic acid may be used in the methods disclosed herein. As such, the sample containing or suspected of containing a target nucleic acid is not specifically limited, and includes, for example, biological samples derived from living subjects, such as whole blood, serum, buffy coat, urine, feces, cerebrospinal fluid, seminal fluid, saliva, tissue (such as cancerous tissue or lymph nodes), cell cultures (such as mammalian cell cultures or bacterial cultures); samples containing nucleic acids, such as viroids, viruses, bacteria, fungi, yeast, plants, and animals; samples (such as food and biological preparations) that may contain or be infected with microorganisms such as viruses or bacteria; and samples that may contain biological substances, such as soil, industrial process and manufacturing equipment, and wastewater; and samples derived from various water sources (e.g., drinking water). Furthermore, a sample may be processed by any known method to prepare a nucleic acid-containing composition used in the methods disclosed herein. Examples of such preparations can include cell breakage (e.g., cell lysates and extracts), sample fractionation, nucleic acids in the samples, and specific nucleic acid molecular groups such as mRNA-enriched samples. The sample used in the method for detecting a target nucleic acid of the present invention is not limited to those derived from biological and natural products as mentioned above and may be a sample containing a synthetic oligonucleotide.

Methods according to the present invention can be performed in combination with the Abbott m2000sp sample preparation system. The m2000sp uses magnetic particle technology to capture nucleic acids and washes the particles to remove unbound sample components. The bound nucleic acids are eluted and transferred to a 96 deep-well plate. The Abbott m2000sp can also combine with the washed nucleic acids transferred to the 96 deep-well plate any reagents required to perform the methods according to the present technology. For example, SC and SA DNAs, polymerases, endonucleases, molecular beacons, and any other reagent (e.g., dNTPs) can be added as required, or desired.

Methods according to the present invention can also be interfaced with point-of-care platforms. For example, the incorporation of a deoxyribonucleotide triphosphate (dNTP) into a growing DNA strand involves the formation of a covalent bond and the release of pyrophosphate and a positively charged hydrogen ion affecting the pH of a reaction. As such, the synthesis of signal DNA according to methods of the present invention can be detected by tracking changes in pH using, for example, point-of-care micro-pH meters. For example, Abbott's i-STAT point-of-care system can be supplied with single-use disposable cartridges containing micro fabricated sensors, calibration solutions, fluidic systems, and waste chambers for analysis of pH.

The methods disclosed herein can comprise additional reagents. Some non-limiting examples of other reagents that can be used in the nucleic acid amplification reaction include metallic salts such as sodium chloride, magnesium chloride, magnesium acetate, and magnesium sulfate; substrates such as dNTP mix; and buffer solutions such as Tris-HCl buffer, tricine buffer, sodium phosphate buffer, and potassium phosphate buffer. Likewise, detergents, oxidants and reducing agents can also be used in the practice of the methods disclosed herein. Furthermore, agents such as dimethyl sulfoxide and betaine (N, N, N-trimethylglycine); acidic substances described in International Publication No. WO 99/54455; and cationic complexes can be used.

The methods and nucleic acid structures provided herein may be used in combination with other methods to provide for the exponential amplification of a signal DNA in the presence of a target nucleic acid. For example, the methods and compositions according to the present disclosure may be used in combination with covered sequence conversion DNAs, as described in U.S. Provisional Application 61/927, 710, entitled "Covered Sequence Conversion DNA and Detection Methods" which is incorporated herein by reference.

The term "about" generally refers to a range of numbers that one of skill in the art would consider equivalent to the recited value (i.e., having the same function or result). The term "about", as used herein, is intended to refer to ranges of approximately 10-20% greater than or less than the referenced value. In certain circumstances, one of skill in the art will recognize that, due to the nature of the referenced value, the term "about" can mean more or less than a 10-20% deviation from that value.

The Examples that follow are intended to be illustrative of the aspects and embodiments described above. Neither the above disclosure nor the Examples below should be viewed as limiting to the scope of the appended claims. One of skill in the art will appreciate that the disclosure is not limited by the particular terminology which is used to describe and illustrate the various aspects of the disclosure.

Example 1

Reactions were performed using SC DNA #246: 5'-AGC-CCTGTACAATGCCCTCAGCCTGTTCCTGCTGAACT-GAGCCA-idT-idT-3' (SEQ ID NO.: 32; bolded positions represent the presence of LNA) and SA DNA #253: 5'-AGC-CCTGTACAATGCCCTCAGCAGCCCTGTACAAT-idT-idT-3' (SEQ ID NO.: 2; bolded positions represent the presence of LNA) to detect the production of signal DNA in the presence of various amounts (1 nM, 100 pM, 10 pM, 1 pM, 100 fM, 10 fM, or 1 fM) or absence of target DNA, which is the same DNA sequence as human hsa-miR-24 (SEQ ID NO.: 33). Both SC DNA #246 and SA DNA #253 were purified using ion exchange HPLC.

The reactions were performed at 37° C. in a 25 µL reaction volume containing New England Biolabs (NEB) Buffer 2 having a final concentration of 10 mM Tris-HCl, 50 mM NaCl, 10 mM MgCl2, 1 mM DTT, pH 7.9. The nicking endonuclease used in the reaction was Nb.BbvCI, which was present at a concentration of 0.1 units/µL. The polymerase used in the reaction was Bst DNA Polymerase Large Fragment, which was present at a concentration of 0.08 units/µL. The dNTPs were present at a final concentration 200 µM each. SC and SA DNAs were present in the reaction at a final concentration of 5 nM and 20 nM, respectively. A Molecular Beacon probe (SEQ ID NO.: 34;) present at a final concentration of 100 nM was used to detect the generation of signal DNA. Fluorescent measurements were performed using a Bio-Rad real-time PCR system CFX96, and the results are shown in Table 1 below.

TABLE 1

| Concentration of Target DNA | Amplification Time (min.) |
|---|---|
| 0 | >138.22 |
| 1 nM | 5.84 |
| 100 pM | 15.03 |
| 10 pM | 32.18 |
| 1 pM | 55.31 |
| 100 fM | 69.68 |
| 10 fM | 73.48 |

Example 2

Reactions were performed at various temperatures (20° C., 25° C., 30° C., 37° C., 45° C., and 50° C.) using SC DNA #246 (SEQ ID NO.: 32) and SA DNA #339 (SEQ ID NO.: 25) to detect the production of signal DNA in the presence (1 nM, 100 pM, 10 pM, 1 pM, 100 fM) or absence of target DNA, which is the same DNA sequence as human hsa-miR-24 (SEQ ID NO.: 33). Both SC DNA #246 and SA DNA #339 were purified using ion exchange HPLC.

Except for temperature, the reaction conditions were as described in Example 1, and the results are shown in Table 2 below.

TABLE 2

| Concentration of Target DNA | Temperature | Amplification Time (min.) |
|---|---|---|
| 0 | 20° C. | >393.32 |
| 1 nM | 20° C. | 109.93 |
| 0 | 25° C. | >393.32 |
| 1 nM | 25° C. | 45.36 |
| 100 pM | 25° C. | 110.75 |
| 10 pM | 25° C. | 244.64 |
| 0 | 30° C. | >393.32 |
| 1 nM | 30° C. | 18.42 |
| 100 pM | 30° C. | 45.58 |
| 10 pM | 30° C. | 105.79 |
| 1 pM | 30° C. | 186.44 |
| 0 | 37° C. | >393.32 |
| 1 nM | 37° C. | 7.59 |
| 100 pM | 37° C. | 19.61 |
| 10 pM | 37° C. | 42.89 |
| 1 pM | 37° C. | 83.07 |
| 100 fM | 37° C. | 120.90 |
| 0 | 45° C. | >393.32 |
| 1 nM | 45° C. | 3.68 |
| 100 pM | 45° C. | 10.07 |
| 10 pM | 45° C. | 25.88 |
| 1 pM | 45° C. | 60.34 |
| 0 | 50° C. | >393.32 |
| 1 nM | 50° C. | 3.65 |

Examples 3 to 38

Further reactions were performed using SC DNA #246 (SEQ ID NO.: 32) together with a number of different SA DNAs (as described below in Table 3), to detect the production of signal DNA in the presence (100 pM) or absence of target DNA, which is the same DNA sequence as human hsa-miR-24 (SEQ ID NO.: 33).

The reaction conditions were as described in Example 1, and the results are as shown in Table 3. The sequence amplification DNA sequence is provided above the Table and indicates the positions (numbered from the 3'-end) that may comprise LNAs.

```
       35   30   25   20   15   10    5    1
        |    |    |    |    |    |    |    |
5'-AGCCC TGTAC AATGC CCTCA GCAGC CCTGT ACAAT-3'
```

TABLE 3

| Ex. # | SA DNA # | SEQ ID NO. | LNA(s) position from 3' end of SA DNA | Amplification Time (min.) 100 pM Target nucleic acid | Amplification Time (min.) 0 pM target nucleic acid | Difference (min.) (0 pM Target) − (100 pm Target) |
|---|---|---|---|---|---|---|
| 3 | 311 | 1 | None | 5.16 | 17.45 | 12.29 |
| 4 | 296 | 2 | 1, 2, 6, 10 | 19.44 | 61.99 | 42.55 |
| 5 | 297 | 3 | 1, 2, 6 | 16.21 | 55.60 | 39.39 |
| 6 | 298 | 4 | 1, 2, 10 | 13.38 | 31.76 | 18.38 |
| 7 | 299 | 5 | 1, 6, 10 | 22.62 | 86.26 | 63.64 |
| 8 | 300 | 6 | 2, 6, 10 | 20.47 | 84.86 | 64.39 |
| 9 | 301 | 7 | 1, 2 | 11.16 | 28.74 | 17.57 |
| 10 | 302 | 8 | 1, 6 | 19.00 | 77.69 | 58.69 |
| 11 | 303 | 9 | 2, 6 | 16.99 | 66.14 | 49.15 |
| 12 | 304 | 10 | 1, 10 | 16.30 | 47.75 | 31.45 |
| 13 | 305 | 11 | 2, 10 | 9.42 | 23.07 | 13.65 |
| 14 | 306 | 12 | 6, 10 | 13.97 | 104.81 | 90.85 |
| 15 | 307 | 13 | 10 | 5.89 | 18.83 | 12.94 |
| 16 | 308 | 14 | 6 | 12.94 | 70.61 | 57.67 |
| 17 | 309 | 15 | 2 | 5.03 | 15.87 | 10.84 |
| 18 | 310 | 16 | 1 | 13.03 | 70.22 | 57.19 |
| 19 | 326 | 2 | 1, 2, 6, 10 | 9.55 | 67.44 | 57.89 |
| 20 | 327 | 13 | 10 | 4.42 | 18.86 | 14.44 |
| 21 | 328 | 17 | 9 | 5.31 | 15.09 | 9.78 |
| 22 | 329 | 18 | 8 | 6.29 | 46.83 | 40.54 |
| 23 | 330 | 19 | 7 | 5.95 | 33.17 | 27.22 |
| 24 | 331 | 14 | 6 | 9.50 | 99.25 | 89.75 |
| 25 | 332 | 20 | 5 | 8.36 | 54.10 | 45.74 |
| 26 | 333 | 21 | 4 | 7.13 | 34.16 | 27.04 |
| 27 | 334 | 22 | 3 | 4.79 | 17.89 | 13.10 |
| 28 | 335 | 15 | 2 | 4.67 | 17.35 | 12.68 |
| 29 | 336 | 16 | 1 | 8.37 | 38.02 | 29.65 |
| 30 | 337 | 23 | 4, 8 | 10.15 | 91.63 | 81.48 |
| 31 | 338 | 24 | 5, 9 | 6.95 | 29.98 | 23.03 |
| 32 | 339 | 25 | 3, 6 | 12.80 | >137.88 | >125.08 |
| 33 | 340 | 26 | 2, 3, 6 | 12.98 | >137.88 | >124.91 |
| 34 | 341 | 27 | 2, 3, 6, 10 | 14.33 | >137.88 | >123.55 |
| 35 | 342 | 28 | 1, 8 | 11.44 | 84.57 | 73.14 |
| 36 | 344 | 29 | 2, 8 | 6.72 | 30.02 | 23.29 |
| 37 | 345 | 30 | 3, 8 | 8.83 | 46.90 | 38.07 |
| 38 | 346 | 31 | 2, 7 | 5.84 | 24.41 | 18.57 |

Examples 39-92

Further reactions were performed using SC DNA #246 (SEQ ID NO.: 32) together with a number of different SA DNAs (as described below in Table 4), to detect the production of signal DNA in the presence (1 nM, 100 pM, 10 pM, 1 pM, and 100 fM) or absence of target DNA, which is the same DNA sequence as human hsa-miR-24 (SEQ ID NO.: 33). As indicated in Table 4, experiments were performed using either unpurified or HPLC purified SA DNA.

The reaction conditions were as described in Example 1, and the results are as shown in Table 4. The sequence amplification DNA sequence is provided above the Table and indicates the positions (numbered from the 3'-end) that may comprise LNAs.

```
       35   30   25   20   15   10    5    1
        |    |    |    |    |    |    |    |
5'-AGCCC TGTAC AATGC CCTCA GCAGC CCTGT ACAAT-3'
```

TABLE 4

| Ex. | SA DNA | SEQ ID NO. | HPLC | LNA(s) position from 3' end of SA DNA | Difference (min.) (0 Target) – (1 nM Target) | Difference (min.) (0 Target) – (100 pM Target) | Difference (min.) (0 Target) – (10 pM Target) | Difference (min.) (0 Target) – (1 pM Target) | Difference (min.) (0 Target) – (100 fM Target) | Difference (min.) (0 Target) – (100 fM Target |
|---|---|---|---|---|---|---|---|---|---|---|
| 39 | 311 | 1 | No | None | 18.23 | 13.86 | 7.05 | 1.70 | 0.12 | −0.46 |
| 40 | 311 | 1 | Yes | None | 24.08 | 20.01 | 14.17 | 9.28 | 1.48 | −1.05 |
| 41 | 296 | 2 | No | 1, 2, 6, 10 | 50.09 | 38.24 | 20.86 | 5.20 | −4.07 | −6.85 |
| 42 | 296 | 2 | Yes | 1, 2, 6, 10 | 110.50 | 101.55 | 77.64 | 40.23 | 23.09 | −0.48 |
| 43 | 298 | 4 | No | 1, 2, 10 | 27.75 | 22.53 | 13.28 | 4.31 | −0.21 | −0.90 |
| 44 | 298 | 4 | Yes | 1, 2, 10 | 27.61 | 23.07 | 14.71 | 5.91 | 0.92 | 0.00 |
| 45 | 299 | 5 | No | 1, 6, 10 | 81.47 | 72.26 | 49.38 | 15.09 | −4.33 | −6.79 |
| 46 | 299 | 5 | Yes | 1, 6, 10 | >133.87 | >123.93 | >94.42 | >38.84 | N/A | N/A |
| 47 | 300 | 6 | No | 2, 6, 10 | 81.75 | 72.64 | 51.27 | 20.57 | −0.52 | −5.63 |
| 48 | 300 | 6 | Yes | 2, 6, 10 | 126.12 | 116.85 | 91.02 | 49.23 | 10.15 | 3.71 |
| 49 | 301 | 7 | No | 1, 2 | 21.48 | 17.60 | 10.33 | 3.31 | 0.23 | −0.74 |
| 50 | 301 | 7 | Yes | 1, 2 | 21.90 | 18.33 | 11.02 | 3.91 | 0.22 | −0.37 |
| 51 | 302 | 8 | No | 1, 6 | 70.60 | 63.23 | 44.93 | 17.96 | 2.91 | −1.32 |
| 52 | 302 | 8 | Yes | 1, 6 | 96.99 | 89.16 | 67.41 | 39.23 | 9.30 | −3.69 |
| 53 | 303 | 9 | No | 2, 6 | 71.73 | 63.60 | 46.48 | 19.67 | 3.76 | 0.38 |
| 54 | 303 | 9 | Yes | 2, 6 | 89.19 | 80.59 | 62.28 | 37.42 | 13.29 | 0.96 |
| 55 | 304 | 10 | No | 1, 10 | 53.87 | 44.92 | 29.13 | 9.88 | 2.10 | 1.23 |
| 56 | 304 | 10 | Yes | 1, 10 | 70.68 | 61.59 | 45.79 | 25.84 | 7.74 | −0.20 |
| 57 | 305 | 11 | No | 2, 10 | 18.67 | 14.10 | 8.68 | 3.08 | 0.39 | 0.57 |
| 58 | 305 | 11 | Yes | 2, 10 | 22.25 | 18.32 | 13.48 | 7.21 | 2.49 | −0.57 |
| 59 | 306 | 12 | No | 6, 10 | 92.07 | 80.17 | 54.53 | 13.19 | 2.27 | 4.15 |
| 60 | 306 | 12 | Yes | 6, 10 | >133.30 | >120.41 | >88.18 | >24.20 | N/A | N/A |
| 61 | 307 | 13 | No | 10 | 21.95 | 17.15 | 9.96 | 2.02 | 0.69 | 0.38 |
| 62 | 307 | 13 | Yes | 10 | 25.99 | 21.80 | 16.71 | 8.38 | 2.06 | 1.42 |
| 63 | 308 | 14 | No | 6 | 65.98 | 56.79 | 36.08 | 7.00 | 3.18 | 0.47 |
| 64 | 308 | 14 | Yes | 6 | 117.75 | 108.40 | 85.99 | 44.28 | 8.00 | −3.17 |
| 65 | 309 | 15 | No | 2 | 17.04 | 13.92 | 8.15 | 2.50 | 0.08 | −0.08 |
| 66 | 309 | 15 | Yes | 2 | 20.43 | 18.22 | 12.59 | 7.62 | 2.23 | 1.09 |
| 67 | 310 | 16 | No | 1 | 37.55 | 30.61 | 16.68 | 4.85 | 0.04 | −0.06 |
| 68 | 310 | 16 | Yes | 1 | 50.77 | 44.61 | 32.67 | 18.37 | 6.27 | 1.60 |
| 69 | 326 | 2 | No | 1, 2, 6, 10 | 66.95 | 56.25 | 34.00 | 12.44 | 5.24 | 2.03 |
| 70 | 326 | 2 | Yes | 1, 2, 6, 10 | 103.95 | 92.33 | 67.10 | 36.34 | 1.75 | −0.24 |
| 71 | 327 | 13 | No | 10 | 24.95 | 20.71 | 13.02 | 5.84 | 0.87 | −0.15 |
| 72 | 327 | 13 | Yes | 10 | 25.31 | 21.25 | 14.95 | 8.91 | 2.89 | 0.35 |
| 73 | 328 | 17 | No | 9 | 15.05 | 11.92 | 6.84 | 2.26 | 0.24 | −0.20 |
| 74 | 328 | 17 | Yes | 9 | 20.53 | 17.38 | 12.21 | 7.25 | 2.93 | 0.56 |
| 75 | 329 | 18 | No | 8 | 61.98 | 54.25 | 37.98 | 23.51 | 16.85 | 14.40 |
| 76 | 329 | 18 | Yes | 8 | 63.53 | 56.82 | 42.94 | 27.45 | 13.69 | 5.17 |
| 77 | 330 | 19 | No | 7 | 36.79 | 31.21 | 20.02 | 8.36 | 2.40 | 0.86 |
| 78 | 330 | 19 | Yes | 7 | 50.62 | 44.32 | 32.65 | 20.78 | 4.03 | 0.05 |
| 79 | 331 | 14 | No | 6 | 106.33 | 95.63 | 71.62 | 30.73 | 6.38 | 0.44 |
| 80 | 331 | 14 | Yes | 6 | 122.99 | 111.94 | 85.44 | 40.13 | 9.04 | 0.00 |
| 81 | 332 | 20 | No | 5 | 69.31 | 60.27 | 42.72 | 19.21 | 4.02 | 0.31 |
| 82 | 332 | 20 | Yes | 5 | 78.59 | 69.51 | 51.76 | 26.48 | 5.25 | −1.48 |
| 83 | 333 | 21 | No | 4 | 40.90 | 33.09 | 21.21 | 9.29 | 1.97 | 0.05 |
| 84 | 333 | 21 | Yes | 4 | 52.10 | 44.17 | 33.30 | 21.03 | 8.37 | 1.80 |
| 85 | 334 | 22 | No | 3 | 23.34 | 17.95 | 11.50 | 4.68 | 0.61 | 0.49 |
| 86 | 334 | 22 | Yes | 3 | 31.21 | 26.09 | 18.85 | 10.91 | 3.83 | 0.28 |
| 87 | 335 | 15 | No | 2 | 21.21 | 17.85 | 9.96 | 3.44 | −0.68 | −0.07 |
| 88 | 335 | 15 | Yes | 2 | 21.33 | 18.31 | 12.00 | 8.21 | 1.06 | −1.79 |
| 89 | 336 | 16 | No | 1 | 41.11 | 33.90 | 21.81 | 8.70 | 2.53 | 0.85 |
| 90 | 336 | 16 | Yes | 1 | 50.65 | 43.87 | 31.68 | 18.42 | 5.77 | 0.96 |
| 91 | 339 | 25 | No | 3, 6 | 164.66 | 155.83 | 125.30 | 68.44 | 17.49 | −1.41 |
| 92 | 339 | 25 | Yes | 3, 6 | >246.97 | >237.39 | >202.59 | >128.53 | >28.94 | N/A |

While the application has been described with reference to certain aspects and embodiments, it will be understood by those skilled in the art that changes may be made to the disclosure provided herein, and equivalents may be substituted without departing from the scope of the disclosure. Accordingly, the application should not be limited to the particular aspects and embodiments disclosed, but should be understood and appreciated to include all aspect and embodiments falling within the scope of the appended claims.

The invention claimed is:

1. A method for detecting a target nucleic acid in a sample, said method comprising contacting said sample with:
   - a first oligonucleotide comprising, in the 5' to 3' direction, a signal DNA generation sequence, an endonuclease recognition site, and a sequence complementary to the 3' end of said target nucleic acid and that comprises a locked nucleic acid;
   - a second oligonucleotide comprising, in the 5' to 3' direction, a signal DNA generation sequence homologous to and capable of hybridizing to the complementary sequence of the signal DNA generation sequence of the first oligonucleotide, an endonuclease recognition site, and a sequence that is homologous to and capable of hybridizing to the complementary sequence of the signal DNA generation sequence of the first oligonucleotide and that comprises a locked nucleic acid;
   - a polymerase; and
   - an endonuclease for a nicking reaction;
   to form a reaction mixture;

maintaining the reaction mixture under conditions that
   allow the target nucleic acid to bind to said first oligonucleotide at said sequence complementary to the 3' end of the target nucleic acid, wherein upon binding, the 3' end of the target nucleic acid primes replication to produce an extended target nucleic acid sequence comprising the complementary sequence to the endonuclease recognition site and the signal DNA generation sequence; and
   allow the endonuclease to produce a nick in the extended target nucleic acid, which primes replication to produce a signal DNA comprising sequence complementary to the signal DNA generation sequence; and
   detecting the signal DNA, wherein the presence of the signal DNA detects the target nucleic acid.

2. The method of claim 1, wherein said locked nucleic acid is located at position 1, 2, 3, 4, 5, 6, 7, 8, 9, 10, or a combination thereof from the 3' end of said second oligonucleotide.

3. The method of claim 1, wherein said second oligonucleotide comprises 2, 3, or 4 locked nucleic acids.

4. The method of claim 3, wherein said locked nucleic acid is located at positions 3 and 6 from the 3' end of said second oligonucleotide.

5. The method of claim 1, wherein said method is performed at a substantially constant temperature.

6. The method of claim 1, wherein said method is performed at a temperature of from about 20° C. to about 42° C.

7. The method of claim 1, wherein said polymerase has strand displacement activity.

8. The method of claim 1, wherein said polymerase is 3' to 5' exonuclease deficient, 5' to 3' exonuclease deficient, or both.

9. The method of claim 1 wherein said target is a micro-RNA.

10. The method of claim 1 wherein said target nucleic acid originates from an infectious agent.

* * * * *

SEQUENCE LISTING

<160> NUMBER OF SEQ ID NOS: 35

<210> SEQ ID NO 1
<211> LENGTH: 35
<212> TYPE: DNA

```
<213> ORGANISM: Artificial Sequence
<220> FEATURE:
<223> OTHER INFORMATION: Signal amplification DNA
<220> FEATURE:
<221> NAME/KEY: misc_feature
<222> LOCATION: (35)..(35)
<223> OTHER INFORMATION: 3'-end modification: two inverted thymidines

<400> SEQUENCE: 1
agccctgtac aatgccctca gcagccctgt acaat                              35

<210> SEQ ID NO 2
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at positions 26, 30, 34, 35
<220> FEATURE:
<221> NAME/KEY: modified_base
<222> LOCATION: (26)..(26)
<223> OTHER INFORMATION: LNA modified base
<220> FEATURE:
<221> NAME/KEY: modified_base
<222> LOCATION: (30)..(30)
<223> OTHER INFORMATION: LNA modified base
<220> FEATURE:
<221> NAME/KEY: modified_base
<222> LOCATION: (34)..(34)
<223> OTHER INFORMATION: LNA modified base
<220> FEATURE:
<221> NAME/KEY: modified_base
<222> LOCATION: (35)..(35)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 2
agccctgtac aatgccctca gcagccctgt acaat                              35

<210> SEQ ID NO 3
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at positions 30, 34, 35
<220> FEATURE:
<221> NAME/KEY: modified_base
<222> LOCATION: (30)..(30)
<223> OTHER INFORMATION: LNA modified base
<220> FEATURE:
<221> NAME/KEY: modified_base
<222> LOCATION: (34)..(34)
<223> OTHER INFORMATION: LNA modified base
<220> FEATURE:
<221> NAME/KEY: modified_base
<222> LOCATION: (35)..(35)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 3
agccctgtac aatgccctca gcagccctgt acaat                              35

<210> SEQ ID NO 4
<211> LENGTH: 35
<212> TYPE: DNA
<213> ORGANISM: Artificial Sequence
```

```
<220> FEATURE:
<223> OTHER INFORMATION: Signal amplification DNA having a locked
      nucleic acid at positions 26, 34, 35
<220> FEATURE:
<221> NAME/KEY: modified_base
<222> LOCATION: (26)..(26)
<223> OTHER INFORMATION: LNA modified base
<220> FEATURE:
<221> NAME/KEY: modified_base
<222> LOCATION: (34)..(34)
<223> OTHER INFORMATION: LNA modified base
<220> FEATURE:
<221> NAME/KEY: modified_base
<222> LOCATION: (35)..(35)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 4
agccctgtac aatgccctca gcagccctgt acaat                              35

<210> SEQ ID NO 5
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at positions 26, 30, 35
<220> FEATURE:
<221> NAME/KEY: modified_base
<222> LOCATION: (26)..(26)
<223> OTHER INFORMATION: LNA modified base
<220> FEATURE:
<221> NAME/KEY: modified_base
<222> LOCATION: (30)..(30)
<223> OTHER INFORMATION: LNA modified base
<220> FEATURE:
<221> NAME/KEY: modified_base
<222> LOCATION: (35)..(35)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 5
agccctgtac aatgccctca gcagccctgt acaat                              35

<210> SEQ ID NO 6
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at positions 26, 30, 34
<220> FEATURE:
<221> NAME/KEY: modified_base
<222> LOCATION: (26)..(26)
<223> OTHER INFORMATION: LNA modified base
<220> FEATURE:
<221> NAME/KEY: modified_base
<222> LOCATION: (30)..(30)
<223> OTHER INFORMATION: LNA modified base
<220> FEATURE:
<221> NAME/KEY: modified_base
<222> LOCATION: (34)..(34)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 6
```
agccctgtac aatgccctca gcagccctgt acaat    35

<210> SEQ ID NO 7
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at positions 34, 35
<220> FEATURE:
<221> NAME/KEY: modified_base
<222> LOCATION: (34)..(34)
<223> OTHER INFORMATION: LNA modified base
<220> FEATURE:
<221> NAME/KEY: modified_base
<222> LOCATION: (35)..(35)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 7
agccctgtac aatgccctca gcagccctgt acaat    35

<210> SEQ ID NO 8
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at positions 30, 35
<220> FEATURE:
<221> NAME/KEY: modified_base
<222> LOCATION: (30)..(30)
<223> OTHER INFORMATION: LNA modified base
<220> FEATURE:
<221> NAME/KEY: modified_base
<222> LOCATION: (35)..(35)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 8
agccctgtac aatgccctca gcagccctgt acaat    35

<210> SEQ ID NO 9
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at positions 30, 34
<220> FEATURE:
<221> NAME/KEY: modified_base
<222> LOCATION: (30)..(30)
<223> OTHER INFORMATION: LNA modified base
<220> FEATURE:
<221> NAME/KEY: modified_base
<222> LOCATION: (34)..(34)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 9
agccctgtac aatgccctca gcagccctgt acaat    35

```
<210> SEQ ID NO 10
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at positions 26, 35
<220> FEATURE:
<221> NAME/KEY: modified_base
<222> LOCATION: (26)..(26)
<223> OTHER INFORMATION: LNA modified base
<220> FEATURE:
<221> NAME/KEY: modified_base
<222> LOCATION: (35)..(35)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 10
agccctgtac aatgccctca gcagccctgt acaat                                35

<210> SEQ ID NO 11
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at positions 26, 34
<220> FEATURE:
<221> NAME/KEY: modified_base
<222> LOCATION: (26)..(26)
<223> OTHER INFORMATION: LNA modified base
<220> FEATURE:
<221> NAME/KEY: modified_base
<222> LOCATION: (34)..(34)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 11
agccctgtac aatgccctca gcagccctgt acaat                                35

<210> SEQ ID NO 12
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at positions 26, 30
<220> FEATURE:
<221> NAME/KEY: modified_base
<222> LOCATION: (26)..(26)
<223> OTHER INFORMATION: LNA modified base
<220> FEATURE:
<221> NAME/KEY: modified_base
<222> LOCATION: (30)..(30)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 12
agccctgtac aatgccctca gcagccctgt acaat                                35

<210> SEQ ID NO 13
<211> LENGTH: 35
<212> TYPE: DNA
<213> ORGANISM: Artificial Sequence
```

```
<220> FEATURE:
<223> OTHER INFORMATION: Signal amplification DNA having a locked
      nucleic acid at position 26
<220> FEATURE:
<221> NAME/KEY: modified_base
<222> LOCATION: (26)..(26)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 13
agccctgtac aatgccctca gcagccctgt acaat                              35

<210> SEQ ID NO 14
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at position 30
<220> FEATURE:
<221> NAME/KEY: modified_base
<222> LOCATION: (30)..(30)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 14
agccctgtac aatgccctca gcagccctgt acaat                              35

<210> SEQ ID NO 15
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at position 34
<220> FEATURE:
<221> NAME/KEY: modified_base
<222> LOCATION: (34)..(34)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 15
agccctgtac aatgccctca gcagccctgt acaat                              35

<210> SEQ ID NO 16
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at position 35
<220> FEATURE:
<221> NAME/KEY: modified_base
<222> LOCATION: (35)..(35)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 16
agccctgtac aatgccctca gcagccctgt acaat                              35
```

<210> SEQ ID NO 17
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at position 27
<220> FEATURE:
<221> NAME/KEY: modified_base
<222> LOCATION: (27)..(27)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 17
agccctgtac aatgccctca gcagccctgt acaat                                35

<210> SEQ ID NO 18
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at position 28
<220> FEATURE:
<221> NAME/KEY: modified_base
<222> LOCATION: (28)..(28)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 18
agccctgtac aatgccctca gcagccctgt acaat                                35

<210> SEQ ID NO 19
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at position 29
<220> FEATURE:
<221> NAME/KEY: modified_base
<222> LOCATION: (29)..(29)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 19
agccctgtac aatgccctca gcagccctgt acaat                                35

<210> SEQ ID NO 20
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at position 31
<220> FEATURE:
<221> NAME/KEY: modified_base
<222> LOCATION: (31)..(31)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 20
agccctgtac aatgccctca gcagccctgt acaat                                    35

<210> SEQ ID NO 21
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at position 32
<220> FEATURE:
<221> NAME/KEY: modified_base
<222> LOCATION: (32)..(32)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 21
agccctgtac aatgccctca gcagccctgt acaat                                    35

<210> SEQ ID NO 22
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at position 33
<220> FEATURE:
<221> NAME/KEY: modified_base
<222> LOCATION: (33)..(33)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 22
agccctgtac aatgccctca gcagccctgt acaat                                    35

<210> SEQ ID NO 23
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at positions 28, 32
<220> FEATURE:
<221> NAME/KEY: modified_base
<222> LOCATION: (28)..(28)
<223> OTHER INFORMATION: LNA modified base
<220> FEATURE:
<221> NAME/KEY: modified_base
<222> LOCATION: (32)..(32)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 23
agccctgtac aatgccctca gcagccctgt acaat                                    35

<210> SEQ ID NO 24
<211> LENGTH: 35
<212> TYPE: DNA
<213> ORGANISM: Artificial Sequence
<220> FEATURE:
<223> OTHER INFORMATION: Signal amplification DNA having a locked

```
        nucleic acid at positions 27, 31
<220> FEATURE:
<221> NAME/KEY: modified_base
<222> LOCATION: (27)..(27)
<223> OTHER INFORMATION: LNA modified base
<220> FEATURE:
<221> NAME/KEY: modified_base
<222> LOCATION: (31)..(31)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 24
agccctgtac aatgccctca gcagccctgt acaat                                35

<210> SEQ ID NO 25
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at positions 30, 33
<220> FEATURE:
<221> NAME/KEY: modified_base
<222> LOCATION: (30)..(30)
<223> OTHER INFORMATION: LNA modified base
<220> FEATURE:
<221> NAME/KEY: modified_base
<222> LOCATION: (33)..(33)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 25
agccctgtac aatgccctca gcagccctgt acaat                                35

<210> SEQ ID NO 26
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at positions 30, 33, 34
<220> FEATURE:
<221> NAME/KEY: modified_base
<222> LOCATION: (30)..(30)
<223> OTHER INFORMATION: LNA modified base
<220> FEATURE:
<221> NAME/KEY: modified_base
<222> LOCATION: (33)..(33)
<223> OTHER INFORMATION: LNA modified base
<220> FEATURE:
<221> NAME/KEY: modified_base
<222> LOCATION: (34)..(34)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 26
agccctgtac aatgccctca gcagccctgt acaat                                35

<210> SEQ ID NO 27
<211> LENGTH: 35
<212> TYPE: DNA
<213> ORGANISM: Artificial Sequence
<220> FEATURE:
<223> OTHER INFORMATION: Signal amplification DNA having a locked
``` nucleic acid at positions 26, 30, 33, 34
<220> FEATURE:
<221> NAME/KEY: modified_base
<222> LOCATION: (26)..(26)
<223> OTHER INFORMATION: LNA modified base
<220> FEATURE:
<221> NAME/KEY: modified_base
<222> LOCATION: (30)..(30)
<223> OTHER INFORMATION: LNA modified base
<220> FEATURE:
<221> NAME/KEY: modified_base
<222> LOCATION: (33)..(33)
<223> OTHER INFORMATION: LNA modified base
<220> FEATURE:
<221> NAME/KEY: modified_base
<222> LOCATION: (34)..(34)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 27
agccctgtac aatgccctca gcagccctgt acaat                               35

<210> SEQ ID NO 28
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at positions 28, 35
<220> FEATURE:
<221> NAME/KEY: modified_base
<222> LOCATION: (28)..(28)
<223> OTHER INFORMATION: LNA modified base
<220> FEATURE:
<221> NAME/KEY: modified_base
<222> LOCATION: (35)..(35)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 28
agccctgtac aatgccctca gcagccctgt acaat                               35

<210> SEQ ID NO 29
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at positions 28, 34
<220> FEATURE:
<221> NAME/KEY: modified_base
<222> LOCATION: (28)..(28)
<223> OTHER INFORMATION: LNA modified base
<220> FEATURE:
<221> NAME/KEY: modified_base
<222> LOCATION: (34)..(34)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 29
agccctgtac aatgccctca gcagccctgt acaat                               35

<210> SEQ ID NO 30
<211> LENGTH: 35

<212> TYPE: DNA
<213> ORGANISM: Artificial Sequence
<220> FEATURE:
<223> OTHER INFORMATION: Signal amplification DNA having a locked
      nucleic acid at positions 28, 33
<220> FEATURE:
<221> NAME/KEY: modified_base
<222> LOCATION: (28)..(28)
<223> OTHER INFORMATION: LNA modified base
<220> FEATURE:
<221> NAME/KEY: modified_base
<222> LOCATION: (33)..(33)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 30
agccctgtac aatgccctca gcagccctgt acaat                              35

<210> SEQ ID NO 31
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at positions 29, 34
<220> FEATURE:
<221> NAME/KEY: modified_base
<222> LOCATION: (29)..(29)
<223> OTHER INFORMATION: LNA modified base
<220> FEATURE:
<221> NAME/KEY: modified_base
<222> LOCATION: (34)..(34)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 31
agccctgtac aatgccctca gcagccctgt acaat                              35

<210> SEQ ID NO 32
<211> LENGTH: 44
<212> TYPE: DNA
<213> ORGANISM: Artificial Sequence
<220> FEATURE:
<223> OTHER INFORMATION: Sequence converter DNA having a locked nucleic
      acid at positions 30, 38
<220> FEATURE:
<221> NAME/KEY: modified_base
<222> LOCATION: (30)..(30)
<223> OTHER INFORMATION: LNA modified base
<220> FEATURE:
<221> NAME/KEY: modified_base
<222> LOCATION: (38)..(38)
<223> OTHER INFORMATION: LNA modified base
<220> FEATURE:
<221> NAME/KEY: misc_feature
<222> LOCATION: (44)..(44)
<223> OTHER INFORMATION: 3'-end modification: two inverted thymidines

<400> SEQUENCE: 32
agccctgtac aatgccctca gcctgttcct gctgaactga gcca                    44

<210> SEQ ID NO 33
<211> LENGTH: 22
<212> TYPE: DNA
<213> ORGANISM: Artificial Sequence
<220> FEATURE:
<223> OTHER INFORMATION: Same DNA sequence as the human hsa-miR-24

-continued

```
<400> SEQUENCE: 33
tggctcagtt cagcaggaac ag                                              22

<210> SEQ ID NO 34
<211> LENGTH: 19
<212> TYPE: DNA
<213> ORGANISM: Artificial Sequence
<220> FEATURE:
<223> OTHER INFORMATION: Molecular Beacon probe, having 6-carboxy-
      fluorescein at the 5' end, and 4-(4'-dimethylaminophenylazo)
      benzoic acid at the 3' end
<220> FEATURE:
<221> NAME/KEY: misc_feature
<222> LOCATION: (1)..(1)
<223> OTHER INFORMATION: 5' end FAM modification
<220> FEATURE:
<221> NAME/KEY: misc_feature
<222> LOCATION: (19)..(19)
<223> OTHER INFORMATION: 3'-end DABCYL modification

<400> SEQUENCE: 34
agccctgtac aatgcggct                                                  19

<210> SEQ ID NO 35
<211> LENGTH: 35
<212> TYPE: DNA
<213> ORGANISM: Artificial Sequence
<220> FEATURE:
<223> OTHER INFORMATION: Signal amplification DNA having a locked
      nucleic acid at positions 26, 33
<220> FEATURE:
<221> NAME/KEY: modified_base
<222> LOCATION: (26)..(26)
<223> OTHER INFORMATION: LNA modified base
<220> FEATURE:
<221> NAME/KEY: modified_base
<222> LOCATION: (33)..(33)
<223> OTHER INFORMATION: LNA modified base
<220> FEATURE:
<221> NAME/KEY: misc_feature
<222> LOCATION: (35)..(35)
<223> OTHER INFORMATION: 3'-end modification: two inverted thymidines

<400> SEQUENCE: 35
agccctgtac aatgccctca gcagccctgt acaat                                35
```